(12) United States Patent
Prokop et al.

(10) Patent No.: US 10,350,311 B2
(45) Date of Patent: Jul. 16, 2019

(54) IOHEXOL POWDER AND METHOD OF USING THE SAME

(71) Applicant: Otsuka Pharmaceutical Co., Ltd., Tokyo (JP)

(72) Inventors: Jiří Prokop, Praha (CZ); Ivan Hlaváček, Praha (CZ); Petr Zahradník, Chomutov (CZ); Jiří Malinak, Jesenice (CZ)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 241 days.

(21) Appl. No.: 14/638,510

(22) Filed: Mar. 4, 2015

(65) Prior Publication Data
US 2015/0251993 A1 Sep. 10, 2015

Related U.S. Application Data

(60) Provisional application No. 61/947,794, filed on Mar. 4, 2014.

(51) Int. Cl.
*A61K 49/04* (2006.01)
*B01D 3/36* (2006.01)
*A61K 49/00* (2006.01)

(52) U.S. Cl.
CPC ...... *A61K 49/0438* (2013.01); *A61K 49/0002* (2013.01); *B01D 3/36* (2013.01); *Y10T 428/2982* (2015.01)

(58) Field of Classification Search
None
See application file for complete search history.

(56) References Cited

U.S. PATENT DOCUMENTS

| | | | |
|---|---|---|---|
| 3,368,944 A | 2/1968 | Sandmark et al. | |
| 4,250,113 A | 2/1981 | Nordal et al. | |
| 2009/0048463 A1* | 2/2009 | Galindro | C07C 231/08 564/153 |
| 2009/0143471 A1 | 6/2009 | Petta et al. | |
| 2010/0331567 A1 | 12/2010 | Giovenzana et al. | |
| 2013/0164224 A1 | 6/2013 | Kim et al. | |

FOREIGN PATENT DOCUMENTS

| | | |
|---|---|---|
| EP | 0919540 A1 | 6/1999 |
| JP | S53-21137 A | 2/1978 |
| JP | H11-158136 | 6/1999 |
| JP | 2009-532441 A | 9/2009 |
| RU | 2469997 C2 | 12/2012 |
| WO | WO 98/08804 A1 | 3/1998 |
| WO | WO 02/083623 A1 | 10/2002 |
| WO | WO 2007/013816 A1 | 2/2007 |
| WO | WO 2007/060380 A1 | 5/2007 |
| WO | WO 2013/007557 | 1/2013 |
| WO | WO 2014/036402 A1 | 3/2014 |

OTHER PUBLICATIONS

International Search Report, PCT appl. No. PCT/JP2015/057076, 5 pages (dated Jul. 10, 2015).
Written Opinion of the International Searching Authority, PCT appl. No. PCT/JP2015/057076, 6 pages (dated Jul. 10, 2015).
Blagden, N.; et al. Advanced Drug Delivery Reviews "Crystal Engineering of Active Pharmaceutical Ingredients to Improve Solubility and Dissolution Rates" 2007, 59, 617-630.
Maghsoodi, M. Advanced Pharmaceutical Bulletin "Role of Solvents in Improvement of Dissolution Rate of Drugs: Crystal Habit and Crystal Agglomeration" 2015, 5, 13-18.
Patil, S.; et al. British J. of Pharm. "Research Effect of Solvent and Crystallization Method on Physicochemical Properties of Aceclofenac and Fenofibrate" 2016, 12, 1-8.
El-Yafi, A. K. E-Z.; et al. Asian Journal of Pharmaceutical Sciences "Technical Crystallization for Application in Pharmaceutical Material Engineering" 2015, 10, 283-291.
Office Action for Russian Patent Application No. 2016138434, dated Oct. 15, 2018, 22 pages.
"Iohexol Injection," Revision Bulletin, Sep. 1, 2011, The United States Pharmacopoeial Convention, [Online], <http://www.pharmacopeia.cn/v29240/usp29nf24s0_m41920.html>, Retrieved on Oct. 11, 2018, 2 pages.
Maruzen PLA-NET Corporation, The multi-form phenomenon of medical supplies and the science of crystallization, Sep. 20, 2002, Chapter 9, pp. 305-317.
Office Action for Japanese Application No. 2016-554688, dated Jan. 8, 2019, 11 pages.

* cited by examiner

*Primary Examiner* — Michael G. Hartley
*Assistant Examiner* — Jennifer Lamberski
(74) *Attorney, Agent, or Firm* — Cooley LLP

(57) ABSTRACT

Iohexol particles, contrast agent compositions comprising iohexol particles, methods of preparing iohexol particles, and methods of administering iohexol particles are provided herein. The iohexol particles of the present invention substantially dissolve in water within about 60 seconds when tested using Modified United States Pharmacopeia Method 641.

2 Claims, 16 Drawing Sheets

FIG. 10A

| Iohexol material | code | Spray drying parameters | | | | | Dissolution time (s) | | Particle Size distribution (μm) | | | Bulk density (g/cm3) | Skeletal density (g/cm3) | Interparticle space (% of bulk volume) | Specific surface area m²/g |
|---|---|---|---|---|---|---|---|---|---|---|---|---|---|---|---|
| | | input concentration of iohexol solution %(w/w) | dispersing of liquid by | atomizer rpm | $T_{inlet}$ (°C) | $T_{outlet}$ (°C) | invention | USP | D10 | D50 | D90 | | | | |
| Spray dryed | 032020121/1 (Invention) | 35 | atomizer | 25,000 | 255 | 95 | 60 | 40 | 9 | 14 | 22 | 0.9 | 2 | 56 | 0.5 |
| | 032020121/8 (Invention) | 35 | atomizer | 25,000 | 220 | 115 | 40 | 30 | 7 | 12 | 19 | 0.9 | 2 | 56 | 0.5 |
| | 032020121/9 (Invention) | 35 | atomizer | 25,000 | 220 | 75 | 60 | 40 | 11 | 20 | 35 | 0.9 | 2 | 56 | 0.5 |
| | Conventional Sample 1 | NA | NA | NA | NA | NA | 90 | 90 | 7 | 27 | 61 | 0.9 | 2 | 56 | 0.5 |
| | Conventional Sample 2 | NA | NA | NA | NA | NA | 90 | 60 | 7 | 29 | 66 | 0.9 | 2 | 56 | 0.5 |

IOHEXOL POWDER AND METHOD OF USING THE SAME

CROSS-REFERENCE TO RELATED APPLICATION

This application claims the benefit of priority to U.S. provisional application No. 61/947,794 titled "IOHEXOL POWDER AND METHOD OF USING THE SAME", filed Mar. 4, 2014, the entire disclosure of which is incorporated herein by reference in its entirety.

BACKGROUND OF THE INVENTION

Iohexol is a known contrast agent having the following structure:

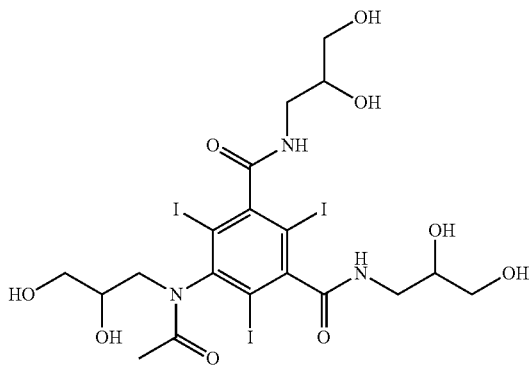 [SMILES: CC(=O)N(CC(O)CO)c1c(I)c(C(=O)NCC(O)CO)c(I)c(C(=O)NCC(O)CO)c1I]

Oral solutions of iohexol are useful as contrast agents for e.g. abdominal imaging by tomography. It is convenient to provide iohexol for such purposes in a solid form which can be reconstituted into an oral contrast solution prior to use. However, although iohexol is highly soluble in water, iohexol particles tend to form large, cohesive, sticky aggregates which dissolve very slowly. Typically, complete dissolution requires extended stirring or elevated temperatures which can lead to degradation of the iohexol in non-buffered systems. Since it is desirable to reconstitute solid (e.g. powdered) iohexol by manually mixing the solid iohexol composition in an appropriate diluent (e.g. water or a flavored aqueous solution) at the physician's office or at an imaging facility, there is a risk that the iohexol composition will not completely dissolve under such conditions, and therefore the patient will receive a lower concentration and dose of the iohexol contrast agent than is desirable for proper imaging. Accordingly, it is important that the iohexol be provided in a form that dissolves rapidly and completely when subjected to manual mixing conditions so that the patient is provided with the full dosage of iohexol, at the proper concentration.

SUMMARY OF THE INVENTION

Compositions and methods are described herein for iohexol. In the various embodiments described herein, the contrast agent composition comprises particles of iohexol that substantially dissolve in water within about 60 seconds or less when tested using a Modified United States Pharmacopeia Method 641 as described herein.

In some embodiments, the contrast agent composition comprises particles of iohexol which have one or more of the following characteristics: a bulk density of less than about 0.8 g/cm$^3$, an interparticle spacing greater than about 60% of bulk volume, and a specific surface area greater than about 0.8 m$^2$/g.

In other embodiments, the contrast agent composition comprises iohexol crystals with a particular crystal structure, for example exhibiting a powder x-ray diffraction pattern substantially as described herein, and having 2θ peaks at about 7.6°, 16.2°, 19.9°, 20.8°, 22.3°, 29.8°, and 30.7°.

In still other embodiments, the contrast agent composition comprises particles of iohexol prepared by a process comprising crystallizing iohexol from a solvent mixture which comprises alcohol, alkyl acetate and water. The crystallization is carried out by heating the solution of iohexol in the solvent mixture (e.g. at reflux) and under vigorous agitation (e.g. stirring) conditions.

In some embodiments, the contrast agent composition comprises iohexol particles with a particle size distribution having one or more of the following characteristics: D90 of no more than about 40 μm, D50 of no more than about 20 μm, and D10 of no more than about 10 μm.

In some embodiments, the contrast agent composition is prepared by spray drying a 30-40% (w/w) solution of iohexol. The inlet temperature of the spray drier falls within the range of about 220-255° C., and the outlet temperature falls within the range of about 95-115° C.

In some embodiments, the method of preparing iohexol crystals includes (a) heating a solution of iohexol in a solvent comprising alcohol, alkyl acetate, and water to reflux, with agitation. The method further includes (b) removing one or more of the alcohol, alkyl acetate, and water by distilling the solution of iohexol. The method further includes (c) maintaining the solution of iohexol with agitation at temperature from 60° C. up to reflux at atmospheric, reduced, or elevated pressure, whereby a suspension of crystals of substantially exo iohexol are formed. The method further includes (d) cooling the suspension of step (b) to about 40-50° C., with agitation, and (e) filtering and drying the suspension.

BRIEF DESCRIPTION OF THE DRAWINGS

FIG. 9B shows the cut surface of one of the spherical particles from FIG. 9A, as indicated by the arrow;

FIG. 10A is a table illustrating the effects of spray drying parameters on dissolution time and particle characteristics;

DETAILED DESCRIPTION

Figure 1:
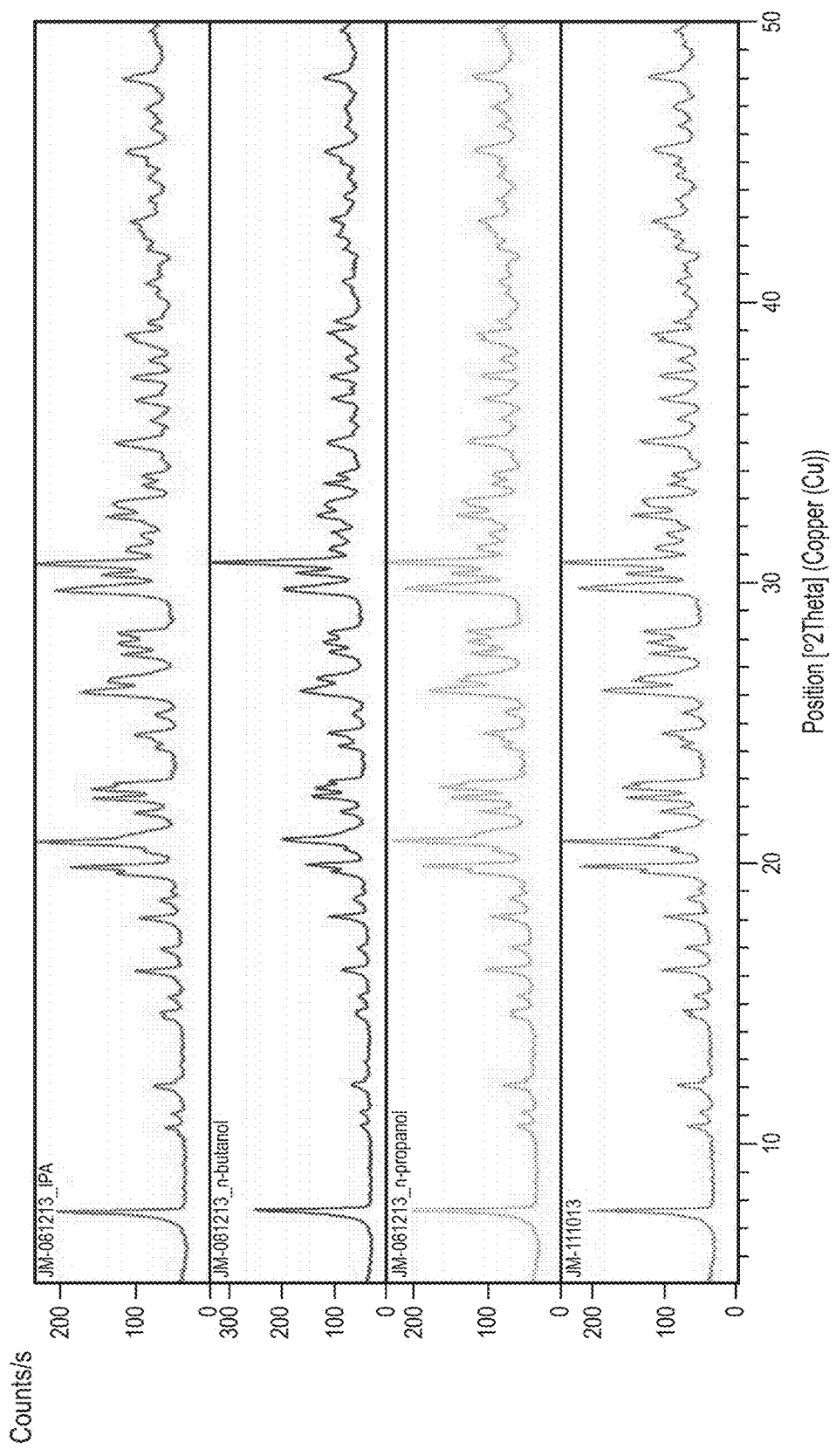
FIG. 1 is a comparison of the x-ray powder diffraction patterns of samples JM-081213_IPA, JM-081213_n-butanol, JM-081213_n-propanol and JM-111013.

Rapidly dissolving compositions of iohexol, and the preparation and use thereof are provided herein. Aspects of the disclosure provide for compositions of iohexol with particular characteristics to enable rapid dissolution including, but not limited to, particle size distribution, particle characteristics, crystalline form and/or the like. Aspects of the disclosure also provide for methods of producing compositions of rapidly dissolving iohexol by the use of particular crystallization or spray drying conditions. All documents, patents, and patent applications cited herein are herein incorporated by reference in their entirety for all purposes.

As used herein, the term "Modified United States Pharmacopeia Method 641" denotes a modified form of the Standard United States Pharmacopeia Method 641, where the Modified United States Pharmacopeia Method 641 is carried out as follows:

Place 1.8 g of the particulate iohexol in a meticulously clean, glass-stoppered, 50 mL glass cylinder approximately 1:10 diameter to height in size.

Fill 40 mL of tap water adjusted to 10° C. (±2° C.) into the glass cylinder.

Immediately start shaking the glass cylinder and start recording total time.

Shake the glass cylinder with an up and down movement, keeping the frequency at 12-13 movements per 5 seconds.

After 20 seconds observe for 3 seconds for completeness of dissolution.

Evaluate after 3 seconds, when the bubbles disappear, comparing with pure solvent.

If dissolved completely, record "dissolved in 20 seconds".

If not dissolved completely, continue shaking for a total time 30 sec

Repeat the dissolution evaluation at 30 seconds, 40 seconds, 1 min., and 1 min. 30 seconds.

Always repeat the dissolution evaluation using the same procedure.

If dissolved completely at time point 1 min 30 sec, record "dissolved in NMT 1 min 30 sec".

If not dissolved, record "not dissolved in 1 min 30 sec".

As used herein, the term "unit dose" denotes a physically identifiable, fixed amount of iohexol, provided for use. However, such fixed, "unit dose" need not comprise the entire amount required for the needs of a given imaging procedure. For example, a given imaging procedure may require more than a unit dose (e.g., multiple unit doses may be combined), or require less than unit dose (e.g., less than the entire amount of iohexol consumed after dissolution in an appropriate diluent).

As used herein, the term "bulk density" of a material denotes total mass of the material divided by the total volume occupied by the material.

As used herein, the term "interparticle spacing" denotes the percentage of the "bulk" particle volume which is free space. The interparticle spacing can be calculated from the bulk density and skeletal density. As discussed above, bulk density refers to the density determined by dividing the weight of the sample by its measured volume, for example using the USP <616> method. The skeletal density, sometimes referred to as the "true density," is determined by dividing the weight of a sample by its "true" volume—i.e., the volume excluding interstitial voids and any open porosity in the sample (e.g., determined by gas displacement techniques). Interparticle spacing can be calculated from the bulk density and skeletal density as exemplified herein: if the bulk density of a particular iohexol sample is ~0.9 g/cm$^3$, the corresponding "bulk" volume for 1 g of the sample is 1.11 cm$^3$; and if the skeletal density of the sample is ~2 g/cm$^3$, the corresponding "skeletal" volume (i.e. volume with porosity excluded) for 1 g of this sample is 0.5 cm$^3$. The difference between the "bulk" volume and "skeletal" volume, 0.61 cm$^3$, represents the volume of the free space (porosity) in the particle. The interparticle spacing is the difference between the "skeletal" volume and bulk volume, divided by the "bulk" volume, expressed as a percentage (i.e. 0.61 cm$^3$/1.11 cm$^3$=55% in this example).

As used herein, the "specific surface area" of a material denotes the total surface area of the material per unit of mass of the material.

As used herein, the "D90" of a particulate material denotes a diameter value for the particles in the material at which about 90% of the particles have a diameter below the diameter value. For example, in a sample with a D90 of 20 μm, 90% of the particles in the sample have a diameter of 20 μm or less.

As used herein, the "D50" of a material denotes a diameter value for the particles in the material at which about 50% of the particles have a diameter below the diameter value. For example, in a sample with a D50 of 10 μm, 50% of the particles in the sample have a diameter of 10 μm or less.

As used herein, the "D10" of a material denotes a diameter value for the particles in the material at which about 10% of the particles have a diameter below the diameter value. For example, in a sample with a D10 of 5 μm, 10% of the particles in the sample have a diameter of 5 μm or less.

As used herein, a "functional excipient or additive" denotes an excipient or additive that increases or enhances the dissolution properties of the iohexol composition, for example, increasing the solubility or dissolution rate of the iohexol. In other words, the rate of dissolution of an iohexol composition with the functional excipient or additive is moderately or substantially higher than that of an otherwise identical iohexol composition without the functional excipient or additive. For example, if the addition of a particular excipient or additive to the contrast agent composition reduces the dissolution time by about 10 or more seconds (e.g., as measured by the Modified USP Method 641 described herein, and as compared to an otherwise identical formulation without the excipient or additive), then such excipient or additive would be considered a "functional excipient or additive." Examples of function excipients and additives include, but are not limited to, disintegrating agents (croscarmellose sodium, crospovidone, carboxymethyl starch, sodium starch glycolate, etc.), dispersants, beta-cyclodextrins and analogs, anticaking agents (e.g. colloidal silicon dioxide, etc.), lubricants (e.g. magnesium stearate, sodium stearyl fumarate, polyethylene glycols, etc.) and so forth.

As used herein, the term "non-functional excipient or additive" denotes an excipient or additive that is not a functional excipient or additive (i.e., does not moderately or substantially increase or enhance the dissolution properties of the iohexol). For example, if the addition of a particular excipient or additive to the contrast agent composition only slightly reduces the dissolution time (e.g., by about 5 seconds or less as measured by the Modified USP Method 641 described herein, and as compared to an otherwise identical formulation without the excipient or additive), or does not change the dissolution time, or increases the dissolution time, then such excipient or additive would be considered a "non-functional excipient or additive." Typically, nonlimiting examples of non-functional excipients or additives include flavoring agents (e.g. sweeteners) or coloring agents, provided such excipients or additives do not enhance the dissolution of the iohexol.

As used herein, the term "sterile" indicates that a substance and/or element has been treated to be and/or is believed to be substantially free of undesirable microorganisms such as, but not limited to, a virus, a bacteria, and/or the like. As used herein, the term "non-sterile" indicates that a substance and/or element has not been treated to be and/or is believed not to be substantially free of undesirable microorganisms such as, but not limited to, a virus, a bacteria, and/or the like.

The term "about" when used in connection with a numerical value means the numerical value, plus or minus up to 15% of that value. For example, "about 100" means from 85 to 115. In other embodiments, term "about" means the referenced numerical value plus or minus up to 10% of that referenced numerical value. For example, "about 100" means from 90 to 110. In particular contexts, the term "about" with regard to a series of numerical values refers to the numerical value, plus or minus half of the interval (without overlap) between the numerical values in the series.

Compositions and methods are described herein for iohexol. In some embodiments, the particles of iohexol of the present invention, e.g., a unit dose of iohexol particles prepared according to the crystallization or spray drying methods described herein, can substantially dissolve in water within about 5 seconds, about 10 seconds, about 20 seconds, about 30 seconds, about 40 seconds, about 50 seconds, about 60 seconds, about 70 seconds, about 80 seconds, or less than about 90 seconds, including all values, ranges, and subranges therebetween, when tested using Modified United States Pharmacopeia Method 641. In some embodiments of the invention, the contrast agent composition includes particles of iohexol that substantially dissolve in water within about 60 seconds when tested using Modified United States Pharmacopeia Method 641. In other embodiments, the particles of iohexol according to the present invention are substantially dissolved within about 40 seconds when tested using Modified United States Pharmacopeia Method 641.

The particles of iohexol according to the present invention can be in crystalline form, in amorphous form, or combinations thereof. In some embodiments, the contrast agent composition of the present invention comprises, consists essentially of, or consists of particles of iohexol in substantially crystalline form. The term "substantially crystalline form" refers to material which is predominantly crystalline, but may contain small amounts of amorphous material (e.g., less than about 1%, less than about 2%, less than about 3%, less than about 4%, less than about 5%, including ranges and subranges therebetween). In other embodiments, the contrast agent composition of the present invention comprises, consists essentially of, or consists of particles of iohexol in substantially amorphous form. Likewise, the term "substantially amorphous form" refers to material which is predominantly amorphous, but may contain small amounts of crystalline material (e.g., less than about 1%, less than about 2%, less than about 3%, less than about 4%, less than about 5%, including ranges and subranges therebetween). In particular embodiments, the crystalline form of iohexol is the specific crystalline form described herein.

In some embodiments, the amount of iohexol provided to a patient for an imaging procedure may be a unit dose, more than a unit dose, or less than a unit dose, depending upon the procedure to be performed (e.g. X-ray procedures, magnetic resonance imaging, and/or the like). In some embodiments, the amount of iohexol in the contrast agent composition is a unit dose. For example, the unit dose can be about 5 g, about 10 g, about 15 g, or about 20 g, inclusive of all values, ranges, and subranges therebetween. In particular embodiments, the amount of iohexol in a unit dose is about 9.7 g.

In some embodiments, the total amount of iohexol provided to a patient can be about 0.2 g, about 0.5 g, about 1.0 g, about 1.5 g, about 2 g, about 3 g, about 5 g, about 10 g, about 15 g, about 20 g, about 30 g, about 40 g, about 50 g, about 60 g, about 65 g, about 70 g, about 75 g, about 80 g, about 85 g, about 90 g, about 100 g, inclusive of all values, ranges, and subranges therebetween. In some embodiments, the amount of iohexol is about 0.1 g. In some embodiments, the amount of iohexol ranges from about 0.2 g to about 75 g. In some embodiments, the amount of iohexol is about 10 g, for example about 9.7 g.

In some embodiments, the contrast agent composition can be substantially free of pharmaceutically acceptable functional excipients, while in other embodiments, the contrast agent composition can include one or more pharmaceutically acceptable functional excipients.

In some embodiments, the contrast agent composition can include at least one pharmaceutically acceptable non-functional excipient, while in other embodiments, the contrast agent composition does not include any pharmaceutically acceptable non-functional excipients.

In some embodiments, the contrast agent composition is substantially free of pharmaceutically acceptable functional excipients. In some embodiments, the contrast agent composition includes at least one pharmaceutically acceptable non-functional excipient.

In some embodiments, the contrast agent composition is substantially free of pharmaceutically acceptable functional excipients and includes at least one pharmaceutically acceptable non-functional excipient.

In various embodiments described herein, the pharmaceutically acceptable non-functional excipient can be selected from the group consisting of dispersants, disintegrants, coatings, fillers, flavors, sorbents, preservatives, sweeteners, coloring agents, wetting agents, binders, anti-caking agents, and combinations thereof, provided that the addition of such excipients does not substantially increase the dissolution of the iohexol as described herein.

The iohexol of the present invention can include the exo isomer of iohexol (also referred to as exo-iohexol), the endo isomer of iohexol (also referred to as endo-iohexol), and any combination thereof. In some embodiments, the iohexol is substantially the exo isomer. In particular embodiments, the iohexol is crystalline and substantially the exo isomer.

In some embodiments, the contrast agent composition can be non-sterile, while in other embodiments, the contrast agent composition can be sterile. In some embodiments, such as when intended for (but not limited to) oral administration for example, the contrast agent composition can be sterile even when sterility is not a requirement. In some embodiments, the contrast agent composition is non-sterile.

The particles of iohexol of the present invention can have any suitable bulk density which provides rapid dissolution. In particular embodiments, the iohexol particles can have a bulk density of about 0.9 $g/cm^3$, about 0.85 $g/cm^3$, about 0.8 $g/cm^3$, about 0.75 $g/cm^3$, about 0.7 $g/cm^3$, about 0.65 $g/cm^3$, about 0.6 $g/cm^3$, about 0.55 $g/cm^3$, about 0.5 $g/cm^3$, about 0.45 $g/cm^3$, about 0.4 $g/cm^3$, about 0.35 $g/cm^3$, about 0.3 $g/cm^3$, about 0.25 $g/cm^3$, or about 0.2 $g/cm^3$, inclusive of all values, ranges, and subranges therebetween. In some embodiments, the iohexol particles have a bulk density of less than about 1 $g/cm^3$. In some embodiments, the particles have a bulk density of less than about 0.8 $g/cm^3$. In some embodiments, the particles have a bulk density of less than about 0.6 $g/cm^3$. In some embodiments, the particles have a bulk density of about 0.6 to about 0.2 $g/cm^3$.

The particles of iohexol can have any suitable interparticle spacing which provides rapid dissolution. In some embodiments, the iohexol particles can have an interparticle spacing of about 50%, about 55%, about 60%, about 65%, about 70% about 75% about 80% about 85% about 90% about 95%, about 96%, about 97%, about 98%, about 99% of bulk volume, inclusive of all values, ranges, and subranges therebetween. In some embodiments, the particles have an interparticle spacing greater than about 40% of bulk volume. In some embodiments, the particles have an interparticle spacing greater than about 60% of bulk volume. In some embodiments, the particles have an interparticle spacing greater than about 70% of bulk volume. In some embodiments, the particles have an interparticle spacing of about 70 to about 95% of bulk volume.

The particles of iohexol can have any suitable specific surface area which provides rapid dissolution. In some embodiments, the iohexol particles can have a specific surface area of about 0.5 $m^2/g$, 0.6 $m^2/g$, about 0.7 $m^2/g$, about 0.8 $m^2/g$, about 0.9 $m^2/g$, about 1 $m^2/g$, about 1.5 $m^2/g$, about 2.0 $m^2/g$, about 2.5 $m^2/g$, about 3 $m^2/g$, about 3.5 $m^2/g$, about 4.0 $m^2/g$, about 4.5 $m^2/g$, about 5.0 $m^2/g$, about 5.5 $m^2/g$, about 6.0 $m^2/g$, about 6.5 $m^2/g$, about 7.0 $m^2/g$, inclusive of all values, ranges, and subranges therebetween. In some embodiments, the particles have a specific surface area greater than about 0.5 $m^2/g$. In some embodiments, the particles have a specific surface area greater than about 0.8 $m^2/g$. In some embodiments, the particles have a specific surface area greater than about 4 $m^2/g$. In some embodiments, the particles have a specific surface area of about 0.8 to about 5 $m^2/g$.

In various embodiments, the particles of iohexol of the present invention have two or more of the bulk density, interparticle spacing, or specific surface area properties described herein above. In yet other embodiments, the particles of iohexol of the present invention have a bulk density, interparticle spacing, and specific surface area property as described herein above. In some embodiments, the particles of iohexol have one or more of the following characteristics: a bulk density of less than about 0.8 $g/cm^3$; an interparticle spacing greater than about 60% of bulk volume; and a specific surface area greater than about 0.8 $m^2/g$.

In some embodiments, the particles have a bulk density less than about 0.8 $g/cm^3$, an interparticle spacing greater than about 60% of bulk volume, and a specific surface area greater than about 0.8 $m^2/g$. In some embodiments, the particles have a bulk density of about 0.6 to about 0.2 $g/cm^3$. In some embodiments, the particles have an interparticle spacing of about 70 to about 95% of bulk volume. In some embodiments, the particles have a specific surface area of about 0.8 to about 5 $m^2/g$. In some embodiments, the particles have a bulk density of about 0.6 to about 0.2 $g/cm^3$, an interparticle spacing of about 70 to about 95% of bulk volume, and a specific surface area of about 0.8 to about 5 $m^2/g$. In some embodiments, the particles have a bulk density of about 0.5 $g/cm^3$, the interparticle spacing is about 70% of bulk volume, and the specific surface area is about 4 $m^2/g$.

In some embodiments, the particles of iohexol comprise iohexol crystals, for example in the form of a crystalline iohexol powder. Such iohexol crystals can be characterized via crystallography techniques, such as (but not limited to) X-ray diffraction, neutron diffraction, electron diffraction, and/or the like. In some embodiments, the iohexol crystals can be characterized by x-ray diffraction patterns, or by one or more lattice parameters, or combinations thereof, for example as described herein.

In some embodiments, the iohexol crystals can have a powder x-ray diffraction pattern substantially identical to those found in FIG. 1, for example having 2θ peaks at about 7.6°, about 10.6°, about 12.1°, about 16.2°, about 18.1°, about 19.7°, about 19.9°, about 20.8°, about 22.3°, about 22.7°, about 22.9°, about 26.1°, about 26.2°, about 29.8°, about 29.9°, about 30.3°, and about 30.7°.

In some embodiments, the iohexol crystals can have the following unit cell parameters at T=293K: a=14.722(3) Å, b=18.921(4) Å, c=9.295(2) Å, α=90°, β=91.281(3°), γ=90°, and a monoclinic P2$_1$/c space group.

In some embodiments, the iohexol crystals have a powder x-ray diffraction pattern having 2θ peaks at about 7.6°, 16.2°, 19.9°, 20.8°, 22.3°, 29.8°, and 30.7°. Additionally, in some embodiments, the iohexol crystals have unit cell parameters at T=293K of: a=14.722(3) Å, b=18.921(4) Å, c=9.295(2) Å, α=90°, β=91.281(3°), γ=90°, and a monoclinic P2$_1$/c space group.

In some embodiments, the iohexol crystals have a powder x-ray diffraction pattern having 2θ peaks at about 7.6°, 10.6°, 12.1°, 16.2°, 18.1°, 19.7°, 19.9°, 20.8°, 22.3°, 22.7°, 22.9°, 26.1°, 26.2°, 29.8°, 29.9°, 30.3°, and 30.7°. Additionally, in some embodiments, the iohexol crystals have unit cell parameters at T=293K of: a=14.722(3) Å, b=18.921(4) Å, c=9.295(2) Å, α=90°, β=91.281(3°), γ=90°, and a monoclinic P2$_1$/c space group.

In some embodiments, the iohexol crystals have unit cell parameters at T=293K of: a=14.722(3) Å, b=18.921(4) Å, c=9.295(2) Å, α=90°, β=91.281(3°), γ=90°, and a monoclinic P2$_1$/c space group.

In some embodiments, the particles of iohexol can be agglomerates of smaller particles, for example agglomerates of smaller nonporous particles.

In some embodiments of the invention, the contrast agent composition comprises particles of iohexol prepared by crystallizing iohexol from a solvent mixture. In some embodiments, the solvent mixture can include one or more solvents selected from alcohol, alkyl ester, and water. In particular embodiments, the solvent mixture comprises alcohol, alkyl ester, and water. In some embodiments, the crystallizing step can be carried out by heating or refluxing the solvent mixture as described herein. In other embodiments, the crystallizing step can be carried out by heating or refluxing the solvent mixture with vigorous mixing.

In various embodiments, the alcohol can be selected from the group consisting of ethanol, 2-propanol, 1-propanol, 1-butanol, and combinations thereof. In various embodiments, the alkyl ester can be selected from the group consisting of methyl acetate, ethyl acetate, propyl acetate, isopropyl acetate, butyl acetate, and combinations thereof.

In various embodiments, the solvent mixture comprises one or more of the alcohols described herein, and one or more of the alkyl esters described herein. In other embodiments, the solvent mixture comprises one or more of the alcohols described herein, one or more of the alkyl esters described herein, and water. In particular embodiments, the solvent mixture comprises ethanol and ethyl acetate. In other particular embodiments, the solvent mixture comprises ethanol, ethyl acetate, and water.

In some embodiments, the solvent mixture can comprise about 90% (w/v) of alcohol, about 91%, about 92%, about 93%, about 94%, about 95%, about 96%, about 97%, about 98%, about 98% of any of the alcohols described herein, inclusive of all values, ranges, and subranges therebetween. In some embodiments, the solvent mixture can comprise about 95-97% (w/v) alcohol. In particular embodiments the solvent mixture comprises about 95-97% (w/v) of ethanol In some embodiments, the solvent mixture can comprise less than about 1% (w/v) of any of the alkyl esters described herein, or can comprise about 1%, about 1.5%, about 2%, about 2.5%, about 3%, about 4%, about 4.5%, about 5%, about 5.5%, about 6%, about 6.5%, about 7%, of the alkyl ester, including all values, ranges, and subranges in between. In some embodiments, the solvent mixture can include about 2-5% (w/v) of alkyl ester.

In some embodiments, the solvent mixture can comprise less than about 0.05% (w/v) of water, or can comprise about 0.08%, about 0.1%, about 0.3%, about 0.5%, about 0.8%, about 1.2%, about 1.6%, about 1.8%, about 2%, about 2.2%, about 2.4%, about 2.8%, about 3%, about 3.5%, of water, inclusive of all values, ranges, and subranges therebetween. In some embodiments, the solvent mixture comprises about 0.1-2% (w/v) of water.

In particular embodiments, the solvent mixture comprises about 95-97% ethanol, about 2-5% alkyl acetate, and about 0.1-2% water.

The method can further include removing at least a portion of one or more of the alcohol, alkyl acetate, and water from the solution of iohexol. In some embodiments, removing at least a portion of the alcohol, alkyl acetate, and/or water can include distillation of the solution of iohexol. In some embodiments, the distillation can be azeotropic distillation. In some embodiments, the method further includes (b) removing at least a portion of one or more of the alcohol, alkyl acetate, and water by distilling the solution of iohexol. The distillation can be carried out under atmospheric pressure, or alternatively under reduced pressure or elevated pressure (relative to atmospheric).

The method can further include maintaining a solution of iohexol with agitation at temperature from about 40° C., about 45° C., about 50° C., about 55° C., about 60° C., about 65° C., about 70° C., about 75° C. to reflux, inclusive of all values, ranges, and subranges therebetween, whereby a suspension of crystals of substantially exo iohexol is formed. The temperature at which the solution of iohexol is maintained can be at atmospheric pressure, or alternatively at reduced or elevated pressures relative to atmospheric pressure. In some embodiments, the method further includes (c) maintaining a solution of iohexol with agitation at temperature from 60° C. up to reflux (at reduced pressure, atmospheric pressure, or elevated pressure), whereby a suspension of crystals of substantially exo iohexol are formed.

The method can further include cooling the suspension of step (b) to about 30° C., about 35° C., about 40° C., about 45° C., about 50° C., about 55° C., about 60° C., including all values, ranges, and subranges in between. The method can include cooling the suspension with or without agitation. In some embodiments, the method further includes (d) cooling the suspension of step (b) to about 40-50° C., with agitation.

The method can further include processing the suspension by one or more processes such as, but not limited to, washing, drying (including vacuum drying), filtering, and/or the like. In some embodiments, the method further includes (e) filtering and drying the suspension. In some embodiments, the distilling can provide a solution (prior to crystallization) having about 10% (w/v) of iohexol, about 15%, about 18%, about 20%, about 22%, about 25%, about 27%, about 30%, about 35% of iohexol, including all values, ranges, and subranges therebetween. In some embodiments, the distilling can provide a solution having about 20-25% (w/v) of iohexol.

In some embodiments, the distilling provides a solution, prior to crystallization, comprising about 20-25% (w/v) of iohexol, about 95-97% alcohol, about 2-5% of alkyl ester, and about 0.1-2% water.

The method can further include maintaining a solution of iohexol (as described herein) with agitation at temperature from about 40° C. to reflux, about 45° C., about 50° C., about 55° C., about 60° C., about 65° C., about 70° C., about 75° C. to reflux, and all values, ranges, and subranges therebetween, whereby a suspension of crystals of substantially exo iohexol are formed. In some embodiments, the method further includes (c) maintaining a solution of iohexol (as described herein) with agitation at temperature from 60° C. up to reflux, whereby a suspension of crystals of substantially exo iohexol are formed.

The method can further include cooling the suspension of step (b) to about 30° C., about 35° C., about 40° C., about 45° C., about 50° C., about 55° C., about 60° C., including all values, ranges, and subranges in between, with agitation. In some embodiments, the method further includes (d) cooling the suspension of step (b) to about 40-50° C., with agitation.

The method can further include processing the suspension by one or more processing such as, but not limited to, washing, drying (including vacuum drying), filtering, and/or the like. In some embodiments, the method further includes (e) filtering and drying the suspension.

In some embodiments of the invention, a contrast agent composition includes iohexol particles with a particular particle size distribution as described herein. For example, the iohexol particle size distribution can have a D90 of about 10 µm, about 11 µm, about 12 µm, about 13 µm, about 14 µm, about 15 µm, about 16 µm, about 17 µm, about 18 µm, about 19 µm, about 20 µm, about 21 µm, about 22 µm, about 23 µm, about 24 µm, about 25 µm, about 26 µm, about 27 µm, about 28 µm, about 29 µm, about 30 µm, about 31 µm, about 32 µm, about 33 µm, about 34 µm, about 35 µm, about 36 µm, about 37 µm, about 38 µm, about 39 µm, or about 40 µm, inclusive of all ranges and subranges therebetween. In some embodiments, the particle size distribution has a D90 of no more than about 40 µm.

In some embodiments, the particle size distribution has a D50 of about 5 µm, about 6 µm, about 7 µm, about 8 µm, about 9 µm, about 10 µm, about 11 µm, about 12 µm, about 13 µm, about 14 µm, about 15 µm, about 16 µm, about 17 µm, about 18 µm, about 19 µm, or about 20 µm, inclusive of all values, ranges and subranges therebetween. In some embodiments, the particle size distribution has a D50 of no more than about 20 µm.

In some embodiments, the particle size distribution has a D10 of about 2 µm, about 3 µm, about 4 µm, about 5 µm, about 6 µm, about 7 µm, about 8 µm, about 9 µm, about 10 µm, or about 12 µm, inclusive of all values, ranges, and subranges therebetween. In some embodiments, the particle size distribution has a D10 of no more than about 11 µm.

In some embodiments, the contrast agent composition comprises iohexol particles with a particle size distribution having one or more of the following characteristics: a D 90 as described herein, a D50 as described herein, and a D10 as described herein. In a particular embodiment, the contrast agent composition comprises iohexol particles with a D90 of no more than about 40 µm; a D50 of no more than about 20 µm; and a D10 of no more than about 10 µm.

In some embodiments, the contrast agent composition can be prepared by spray drying a solution of iohexol using particular spray drying conditions which provide iohexol particles which dissolve rapidly. Any suitable spray dryer configuration can be used, including spray dryers with a nozzle atomizer, centrifugal atomizer, countercurrent and concurrent configurations, etc. In particular, the inlet and outlet temperature of the spray drier affects the dissolution rate of the iohexol particles produced thereby. In such embodiments, the inlet temperature of the spray drier (e.g., for aqueous solutions of iohexol) can be about 200° C., about 210° C., about 215° C., about 220° C., about 230° C., about 240° C., about 245° C., about 250° C., about 255° C., about 260° C., about 270° C., about 280° C., inclusive of all values, ranges, and subranges therebetween. In some embodiments, the inlet temperature of the spray drier can fall within the range of about 220-255° C. In some embodiments, the outlet temperature of the spray drier can be about 70° C., about 80° C., about 85° C., about 90° C., about 95° C., about 100° C., about 105° C., about 110° C., about 115° C., about 120° C., about 130° C., about 140° C., inclusive of all values, ranges, and subranges therebetween. In some embodiments, the outlet temperature of the spray drier can fall within the range of about 95-115° C.

In some embodiments, the contrast agent composition is prepared by spray drying a solution of iohexol. In some embodiments, the inlet temperature of the spray drier falls within the range of about 220-255° C., and the outlet temperature falls within the range of about 95-115° C.

In some embodiments, spray drying the solution of iohexol can include operating the atomizer (e.g. a centrifugal atomizer) of the spray drier at an RPM (revolutions per minute) of about 15,000, about 20,000, about 22,000, about 24,000, about 25,000, about 26,000, about 28,000, about 30,000, about 35,000, and all values, ranges, and subranges in between. In some embodiments, the atomizer RPM is about 25,000. In particular embodiments, the inlet temperature, and outlet temperature, and atomizer conditions are all as described herein.

In some embodiments, the iohexol solution can have a concentration of about 20% (w/w), about 25% (w/w), about 27% (w/w), about 29% (w/w), about 30% (w/w), about 31% (w/w), about 33% (w/w), about 35% (w/w), about 37% (w/w), about 39% (w/w), about 40% (w/w), about 41% (w/w), about 43% (w/w), about 45% (w/w), and all values, ranges, and subranges in between. In some embodiments, the iohexol solution has a concentration of about 30-40% (w/w).

Any suitable solvent suitable for spray drying can be used, provided the iohexol is soluble therein. A non-limiting list of suitable solvents for spray drying iohexol include water, and alcohols such as ethyl alcohol. In other embodiments, mixtures of water with organic solvents (e.g., alcohols and/or alkyl acetates) can be used, wherein the water ensures solubilization of the iohexol until it is spray dried.

In some embodiments of the invention, iohexol particles are prepared by spray drying a 30-40% (w/w) solution of iohexol. In some embodiments, the inlet temperature of the spray drier falls within the range of about 220-255° C., and the outlet temperature falls within the range of about 95-115° C. In other embodiments the spray dried iohexol has the particle size distribution as described herein.

Various embodiments of the invention also include iohexol crystals prepared by any method of preparing iohexol crystals described herein.

Various embodiments of the invention also include a contrast agent composition including iohexol crystals prepared by any method of preparing iohexol crystals described herein.

In some embodiments a method of forming an iohexol contrast solution can include adding a pharmaceutically acceptable aqueous diluent to a container containing any contrast agent composition described herein. In some embodiments, the container can be as described in U.S. patent application Ser. No. 13/934,654, filed Jul. 3, 2013, titled "CONTAINER WITH CONCENTRATED SUBSTANCE AND METHOD OF USING THE SAME", the entire disclosure of which is incorporated by reference herein it its entirety.

The method can further include agitating the container such that substantially all of the iohexol contrast agent is dissolved. In some embodiments, the agitating can be carried out for about 30 seconds, about 35 seconds, about 40 seconds, about 45 seconds, 50 seconds, for about 60 seconds, about 70 seconds, about 80 seconds, about 85 seconds, about 90 seconds, about 95 seconds, about 100 seconds, about 110 seconds, about 120 seconds, about 130 seconds, including all values, ranges, and subranges in between. In some embodiments, the agitating can be carried out for no more than about 90 seconds. In some embodiments, the agitating can be carried out for no more than about 60 seconds. In some embodiments, the agitating can be carried out for no more than about 40 seconds. The agitation can include manual agitation, automated agitation, or any combination thereof. In particular embodiments, the agitation includes manual agitation.

In some embodiments, the method of forming the iohexol contrast solution can include adding a pharmaceutically acceptable aqueous diluent to a container containing a contrast agent composition that includes particles of iohexol that can substantially dissolve in water within about 5 seconds, about 10 seconds, about 20 seconds, about 30 seconds, about 40 seconds, about 50 seconds, about 60 seconds, about 70 seconds, about 80 seconds, and all values, ranges, and subranges in between, when tested using Modified United States Pharmacopeia Method 641. In some embodiments, the method of forming the iohexol contrast solution includes (a) adding a pharmaceutically acceptable aqueous diluent to a container containing a contrast agent composition that includes particles of iohexol that can substantially dissolve in water within about 60 seconds when tested using Modified United States Pharmacopeia Method 641.

The method further can include agitating the container for no more than about 30 seconds, about 35 seconds, about 40 seconds, about 45 seconds, 50 seconds, for about 60 seconds, about 70 seconds, about 80 seconds, about 85 seconds, about 90 seconds, about 95 seconds, about 100 seconds, about 110 seconds, about 120 seconds, about 130 seconds, including all values, ranges, and subranges therebetween. The agitation can include manual agitation, automated agitation, or any combination thereof. In some embodiments, the method further includes (b) agitating the container for no more than about 90 seconds, whereby substantially all of the iohexol contrast agent is dissolved. In some embodiments, step (b) is manual agitation. In some embodiments, the container is manually agitated for no more than about 60 seconds. In some embodiments, the container is manually agitated for no more than about 40 seconds.

Some embodiments of the invention are directed to administering an iohexol contrast solution to a patient in need thereof, such as, for example, prior to an imaging procedure to be performed on the patient. The administering can include preparing an iohexol contrast solution as described herein, and administering the iohexol contrast solution to the patient, for example by oral administration.

In some embodiments, administering an iohexol contrast solution to a patient in need thereof includes (a) adding a pharmaceutically acceptable aqueous diluent to a container containing a contrast agent composition that includes particles of iohexol that substantially dissolve in water within about 60 seconds when tested using Modified United States Pharmacopeia Method 641. The administering further includes (b) agitating the container for no more than 90 seconds, whereby substantially all of the iohexol contrast agent is dissolved. The administering further includes administering the contrast solution to the patient.

In various embodiments, the processes described herein can provide specific shape(s) and particles size(s) and particle size distributions of the iohexol, which in turn can improve the solubility characteristics of the iohexol. For example, the iohexol particles crystallized according to the methods described herein can be characterized as agglomerates of smaller crystals, with high specific surface area. This high specific surface area can enable extensive contact with the diluent during reconstitution of compositions containing such forms of iohexol, resulting in a rapid dissolution rate, without the formation of sticky masses of iohexol in the distillation vessel during the dissolution process. Conventional spray-dried iohexol, which typically forms spherically shaped particles with low surface area, has a poorer (slower) dissolution rate compared to that of the crystallized or spray dried iohexol according to the present invention.

Various of the embodiments disclosed herein provide for iohexol crystallization and preferential formation of exo isomers. In other words, the iohexol formed thereby comprises substantially the exo isomer. Based on observations (see Examples below), exo iohexol has a lower tendency to absorb moisture than naturally occurring iohexol, which typically contains both endo and exo isomers. Each rotational isomer (exo and endo) can have a different crystal structure. It is believed that this difference can lead to a different extent of water penetration into the crystal lattice, resulting in faster dissolution of the exo iohexol isomer. Thus, in embodiments of the present invention in which substantially exo iohexol is provided, more rapid dissolution can be provided compared to conventional formulations comprising a mixture of endo and exo iohexol.

In other embodiments disclosed herein, the ratio of endo and exo isomers of iohexol in the composition can be changed by changing the composition of the solvent mixture used during crystallization, for example, changing the ratio of e.g., water, ethyl acetate, and ethanol used in the crystallization.

Traditionally the preparation and dosing of iodinated contrast media requires the combination of separate components in order to prepare a single dose unit (unit dose) which is delivered to the patient. These components include but are not limited to: a bottle of liquid, concentrated contrast media, a measuring device such as a syringe or other measuring device and one or two cups for dispensing. Embodiments disclosed herein can be useful as part of a self-contained kit for the administration of oral contrast media, where all these components can be provided as part of the kit. The compositions of the present invention can be diluted with various diluents which provide stable solutions suitable for human consumption. These diluents can include, for example, beverages such as lemonade (e.g., powdered lemonade or other fruit flavored beverage mixes), sports drinks (e.g., isotonic sports beverages), a variety of fruit juices, water, infant formula, etc. Such flavored diluents are intended to increase patient compliance (i.e., the likelihood that the patient will finish the entire dose) by masking any unpleasant or objectionable flavor of the iohexol.

EXAMPLES

Example 1

Four powder samples of Iohexol particles were prepared according to the invention for further structural analysis (Table 1)

TABLE 1

| Sample | Crystallized from |
| --- | --- |
| JM-111013 | ethanol |
| JM-081213_IPA | 2-propanol |
| JM-081213_n-propanol | 1-propanol |
| JM-081213_n-butanol | 1-butanol |

Data Collection

Two methods for crystal characterization were used:
a) X-ray powder analysis—small amount of all four samples were measured.
b) X-ray structure determination—a suitable single crystal of iohexol was found in sample JM-081213_n-butanol and directly mounted on goniometer head for the crystal structure determination.

Results
X-Ray Powder Analysis

All four measured samples have similar X-ray powder patterns as shown in FIG. 1. The number of peaks for all four samples in the 2θ range (5-20°, reasonably separated peaks) are similar, and the positions of the peaks can be reasonably determined to be about the same, within experimental error. In accordance with the observed patterns, all four samples appear to have substantially the same crystal structure (see FIG. 1) which are very similar to the powder pattern calculated from the crystal structure data. The relative intensities of the peaks are similar for the samples JM-081213_n-propanol, JM-081213_IPA and JM-111013 and are comparable to those calculated from the crystal structure data.

Unit Cell Parameters for Sample JM-111013

The automatic indexing of results obtained using DICVOLO4 show that the iohexol crystals formed are monoclinic with space group P21/c and the unit-cell parameters were least-square refined to the values:

$a=14.722(3)$ Å, $\alpha=90°$
$b=18.921(4)$ Å, $\beta=91.281(3)°$
$c=9.295(2)$ Å, $\gamma=90°$
Volume: 2589(1) Å$^3$
Crystal Class: monoclinic
Cell determined from: 107 reflections
Cell 2θ range=5-60°
Temperature: 293 K Example 2

Evaluation of Difference in Dissolving Time Between Iohexol Substance Prepared by Different Isolation Techniques Samples
1) Iohexol crystallized according to the invention—two batches, 03302012 and 01206013.
2) Conventional spray-dried iohexol—two batches, labeled Conventional Samples #1 and #2.
4) Iohexol spray-dried according to the invention—batch 03202012/1.
5) Iohexol spray-dried according to the invention, and according to a modified procedure, batch 03202012/8.
6) Iohexol spray-dried according to the invention, and according to a modified procedure, batch 03202012/9.

Materials and Testing Device 20 oz (600 ml) modified beverage PET bottle for Iohexol Powder for Oral Solution product; 50 ml testing glass cylinder; Tap water.

Samples were tested using the Modified USP Method <641> as described herein.

Results

TABLE 4

Results

| Batch No. | Description | Dissolution Time (s) |
|---|---|---|
| 01206013 | crystallized Iohexol | 40 |
| 03302012 | crystallised Iohexol | 40 |
| 03202012/8 | Iohexol spray dried, 220/115° C. | 40 |
| 03202012/1 | Iohexol spray dried, 255/95° C. | 60 |
| 03202012/9 | Iohexol spray dried, 220/75° C. | 60 |
| Conventional Sample #1 | Iohexol USP spray-dried | dissolved in NMT 1 min 30 sec |
| Conventional Sample #2 | Iohexol USP spray-dried | dissolved in NMT 1 min 30 sec |

Iohexol crystallized according to the invention formed very small particles aggregated in clusters, with very large surface area and spacing between the particles. This material dissolved rapidly.

The worst results were provided by conventional, spray-dried iohexol, which provided unsuitable dissolution times of 1 min 30 sec. This material had a lower surface area compared to the crystallized iohexol. In addition, the conventionally spray dried iohexol powder, after pouring water into the bottle, forms a glue-like layer than sticks at the bottom and increases the dissolution time.

Spray dried material was prepared using various conditions: conventional spray drying conditions (input temperature 255° C., output 95° C.), and modified spray drying conditions (input temperature 220° C., output 75° C.; and input temperature 220° C., output 115° C.). The best performance was provided by one of the modified spray drying conditions (input temperature 220° C., output 115° C.) which provided smaller iohexol particles. The improved particle size was provided by the presence of smaller particles overall (D50 around 16 microns) and a very narrow particle size distribution, almost free of particles bigger than 30 microns. In contrast, the particle size distribution prepared by conventional spray drying methods is much wider, with a substantial amount of particles bigger than 30 microns, and a significant amount more than 50 microns.

Example 3

Evaluation of Particle Morphology, Skeletal, Apparent Densities and Specific Surface Areas of Variously Prepared Iohexol The solid iohexol was obtained by crystallization or by spray drying. It was found that the mode of preparation of the solid phase determines the rate of dissolution of the iohexol. Samples are identified as crystallized iohexol or spray dried iohexol. Each type of iohexol was represented by several samples. Some samples were also exposed to the laboratory atmosphere (e.g., ambient air) and then analyzed.

The particle morphology was evaluated by Scanning Electron Microscopy (SEM) combined with ion microscope FIB-SEM Tescan Lyra3GU equipped with a number of detectors EDS, EBSD, STEM, EBIC and TOF-SIMS. Due to the non-conductive nature of iohexol, it accumulates an electrical charge which causes deterioration of SEM images. Therefore, iohexol samples were coated with a thin layer of platinum to remove electrical charges and thereby obtain high quality SEM images.

Specific surface area was measured using a low-temperature nitrogen adsorption apparatus, a Pulse Chemisorb 2700.

Crystallized Iohexol

Figure 2:
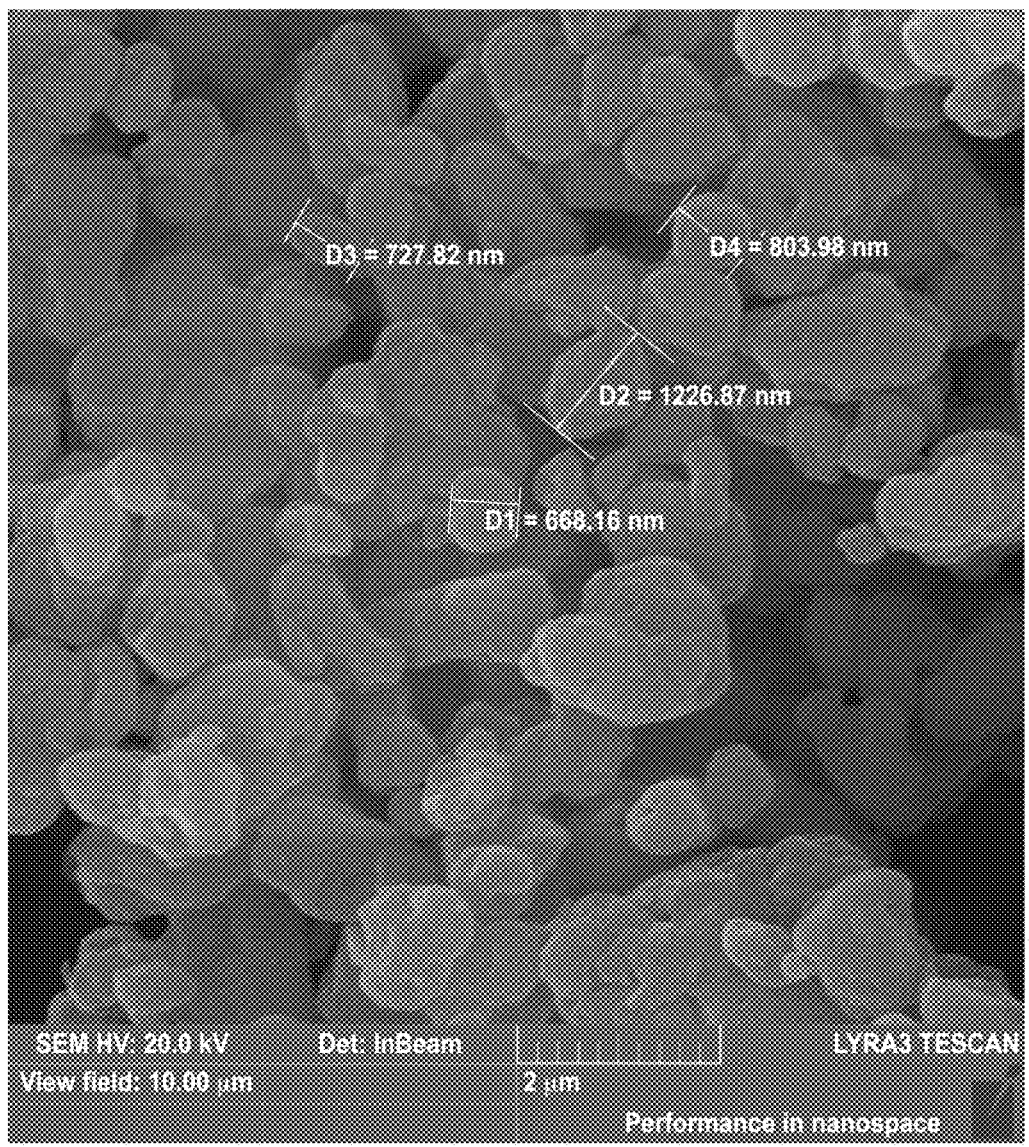
FIG. 2 is an SEM image of iohexol crystals prepared by the crystallization method of the present invention, having a characteristic dimension of the individual particles of approximately 0.5-3 μm.
Figure 3:
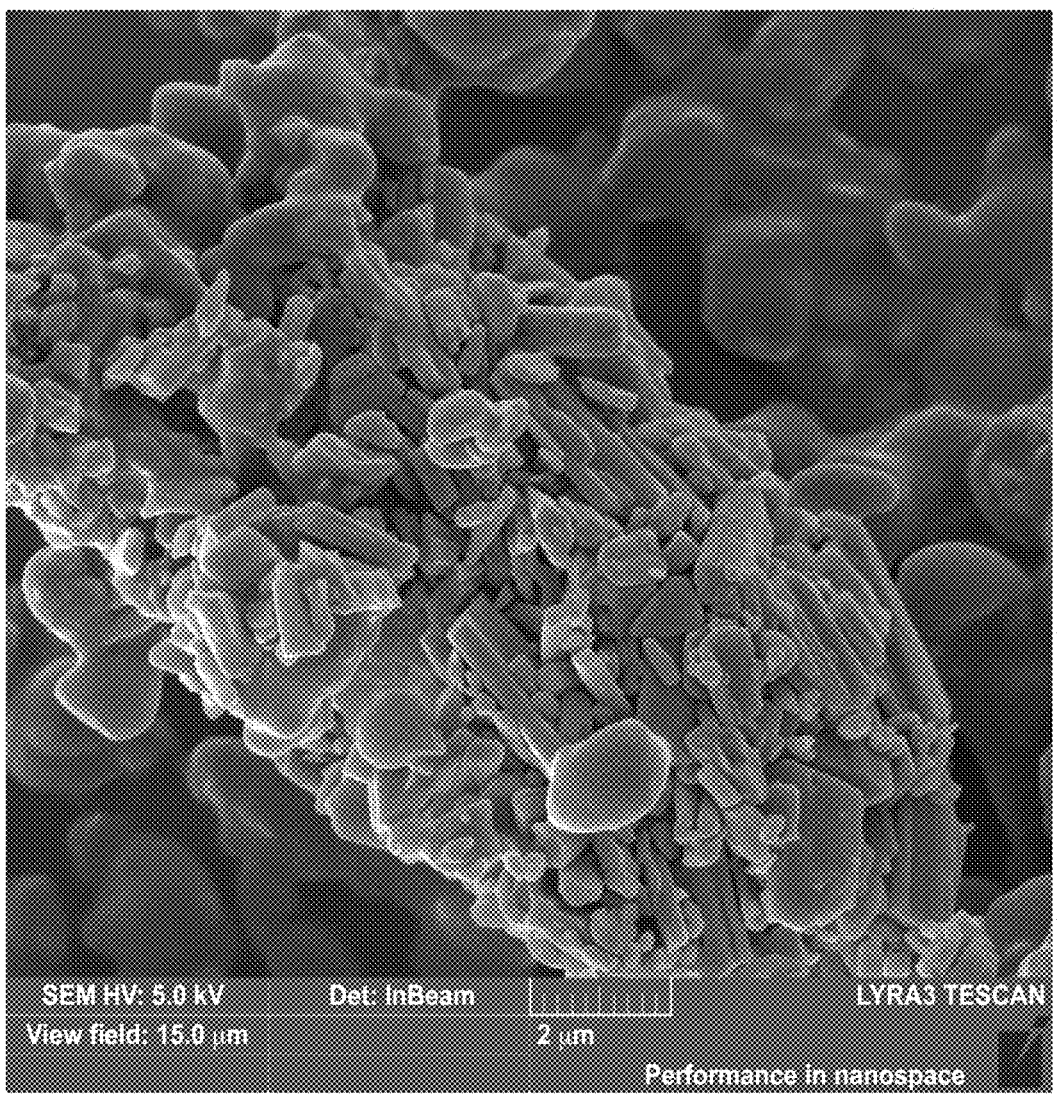
FIG. 3 is an SEM image of iohexol crystals prepared by the crystallization method of the present invention, showing agglomeration of crystals formed in areas with low mixing intensity.
Figure 4:
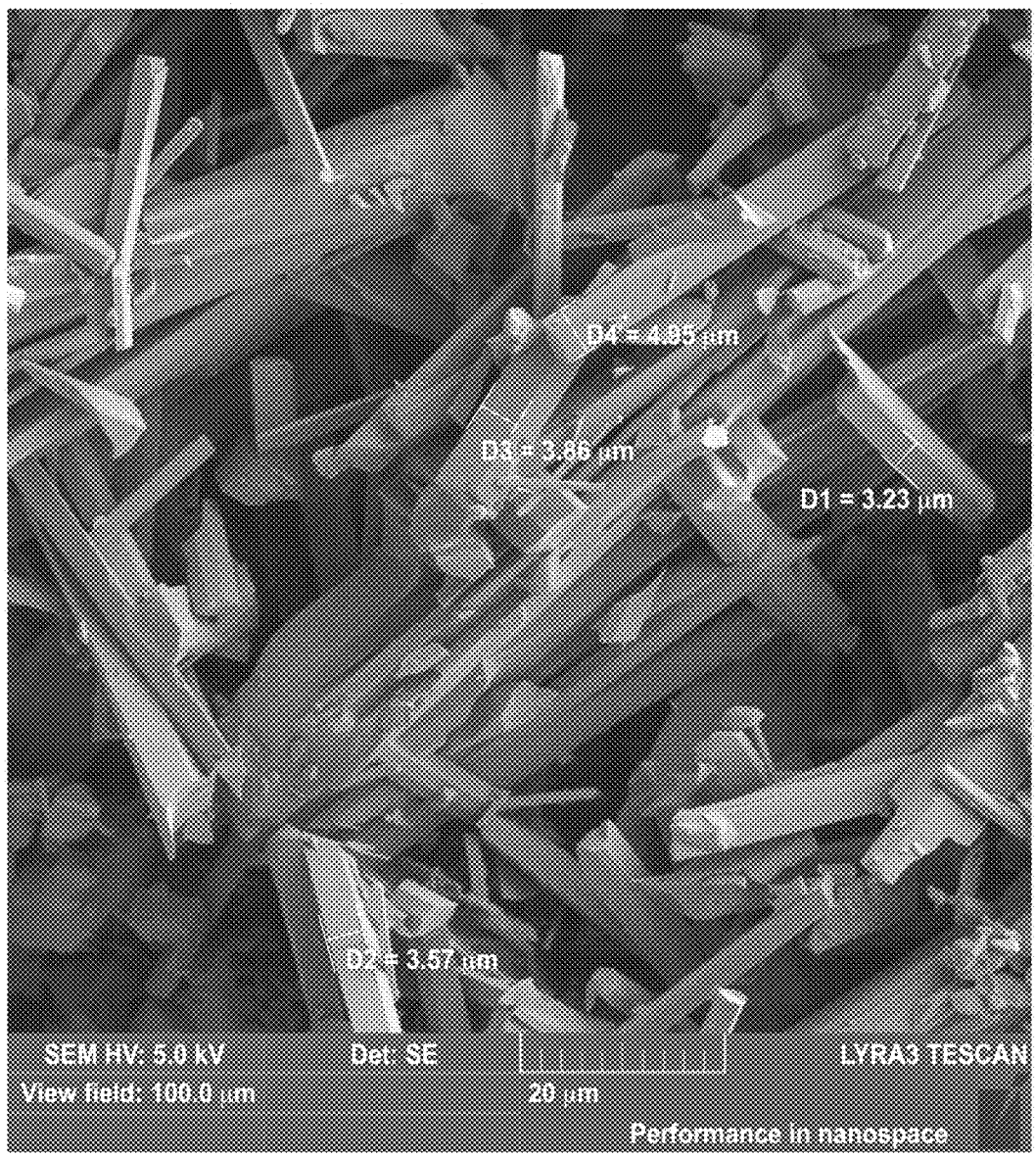
FIG. 4 is an SEM image of iohexol crystals prepared without stirring during crystallization.

SEM images show that crystallized iohexol forms agglomerates of particles of spherical/ellipsoidal shape, in which the characteristic dimension of the individual particles is approximately 0.5-3 μm as shown in FIG. 2. Also, long rod-shape crystals were observed in all samples of crystallized iohexol (FIG. 3). Such rod-shaped particles are believed to be formed in areas of the crystallization vessel with low or zero intensity of mixing. This assumption was confirmed during a crystallization experiment without stirring, when large rod-shaped crystals, with length up to 100 μm and diameter 3-5 μm, were obtained (FIG. 4).

Figure 5:
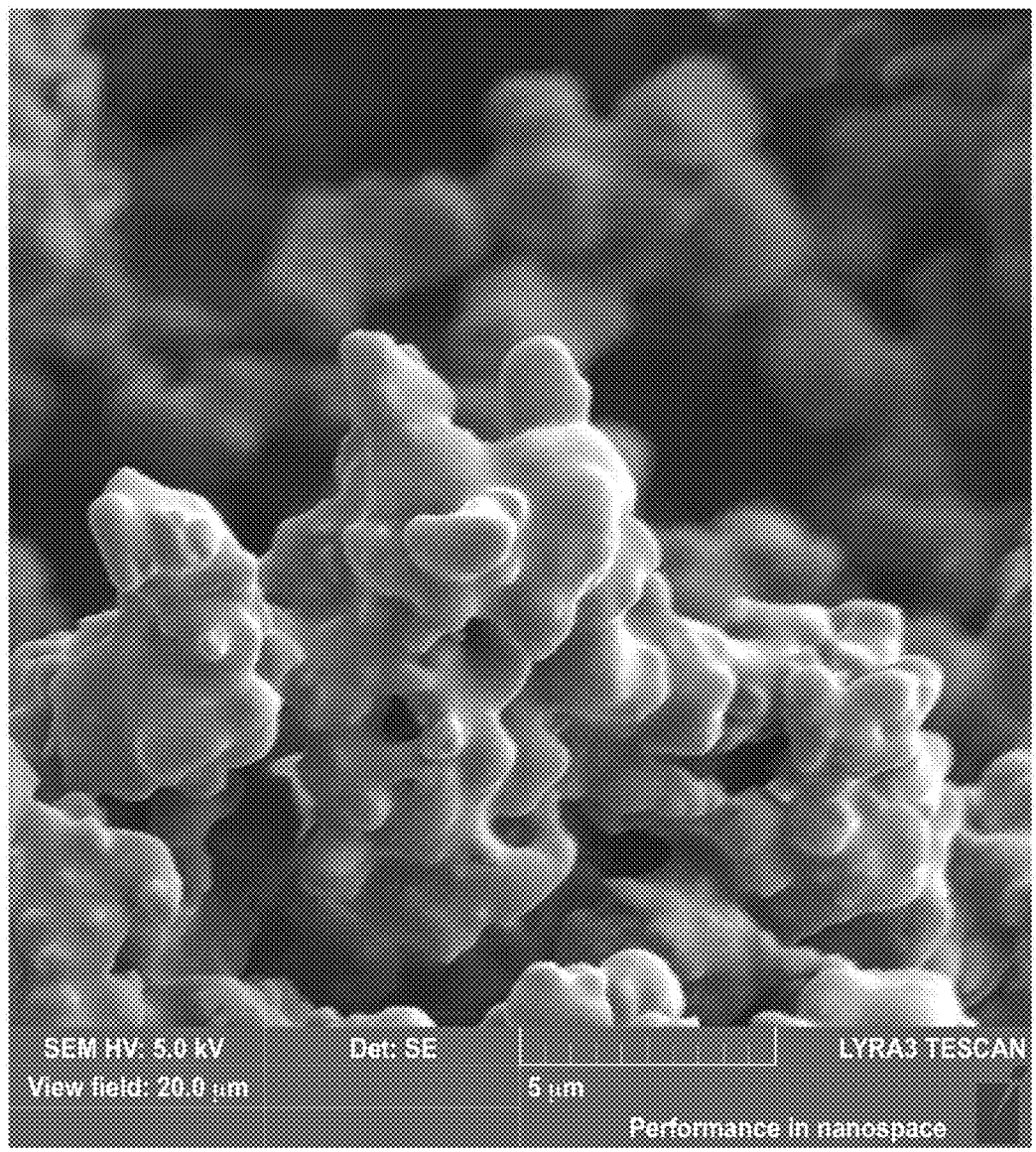
FIG. 5 is an SEM image of iohexol crystals showing the sintering of the particles due to the effects of humidity.

Crystallized iohexol samples were also examined by SME analysis for the influence of air humidity (i.e., humidity of ambient/room air). Crystallized iohexol samples were exposed to air humidity for 120 hours. After this exposure, the sintering of originally separated particles was observed (FIG. 5).

The porosity of the iohexol particles was also investigated using mercury intrusion, and the skeletal density was determined by helium pycnometer and physical adsorption of nitrogen.

Figure 6:
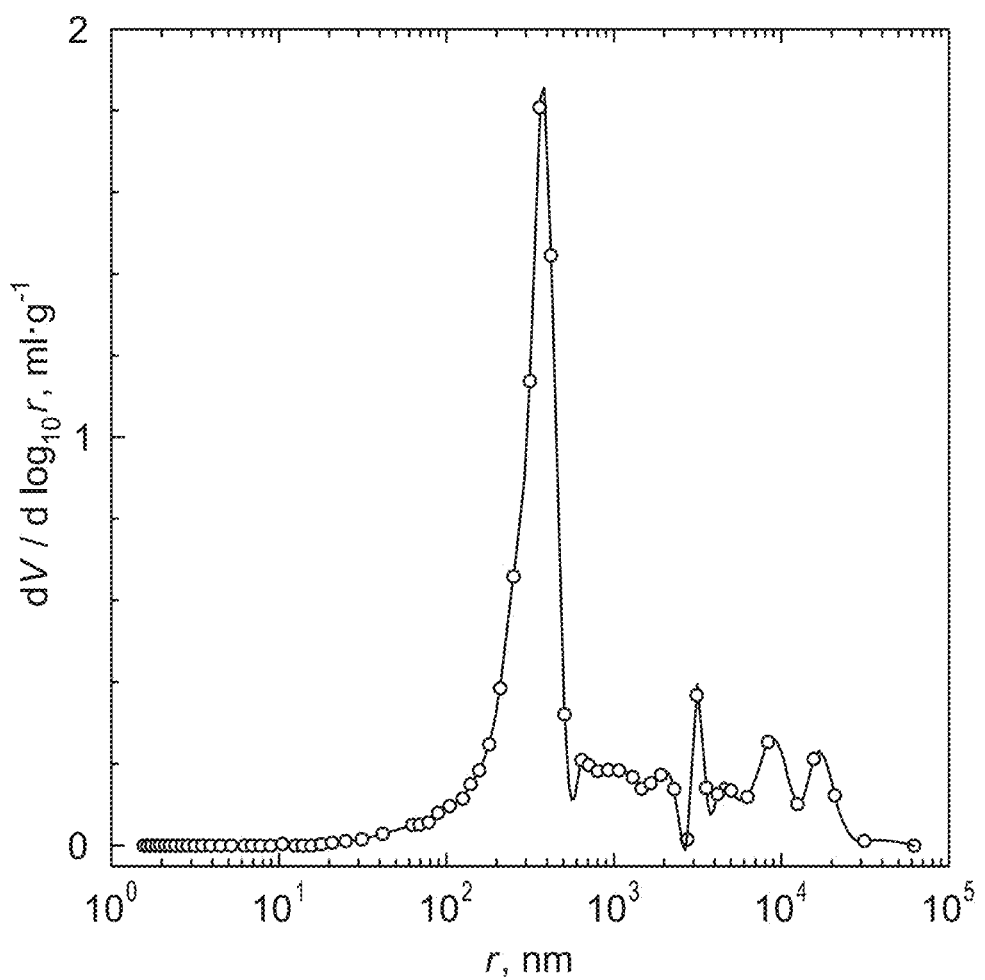
FIG. 6 is a plot of the size distribution of open cavities in crystallized iohexol, obtained by mercury porosimetry—the cavities between agglomerates have an approximate size of between about 1 and about 100 μm.

The particle size distribution obtained by mercury porosimetry (FIG. 6) shows the presence of spaces between the agglomerates, and between particles with the characteristic sizes mentioned above (0.5-3 μm). The cavities between the agglomerates have an approximate size between about 1 and about 100 µm. Since this data was obtained by mercury porosimetry, cavity size can be defined as the radius of a cylindrical pore. Smaller cavities correspond to the spaces between the particles. A significant maxima at 300 nm (see significant peak on FIG. 6) corresponds to the size of the narrowest area (window), when three spherical particles with a radius approximately 3 µm are in contact. A further increase of embossed mercury under higher pressures was not observed. This finding excludes the presence of very small, open cavities or pores, and therefore it is assumed that the small particles are not porous.

The specific surface area data, which were evaluated using a BET isotherm, support the nonporous nature/character of the particles. The measured value of the specific surface area was about 2.8 m$^2$/g, which is consistent with the calculation of the specific surface area of hypothetical material which consists of non-porous spheres with a radius of 3 µm. Considering the skeletal density of crystallized iohexol (2.097 g/cm3), the calculated specific surface area of this hypothetical material is about 4 m$^2$/g. All data provided by analyses appear to support the conclusion that the crystallized iohexol solid material contains agglomerates consisting of small nonporous particles and that the total specific area is the sum of the outer surface areas of these particles.

Spray Dried Iohexol

Three different samples of spray dried iohexol were selected for evaluation:
1) Spray dried iohexol produced according to the invention using the spray drying conditions described above in Example 2 (batch number 00405003).
2) Conventional spray dried iohexol (Conventional Sample #2).
3) Freshly produced spray dried iohexol (batch number 03202012/1) according to the present invention, produced using the same conditions as used for sample number 00405003, above.

Figure 7:
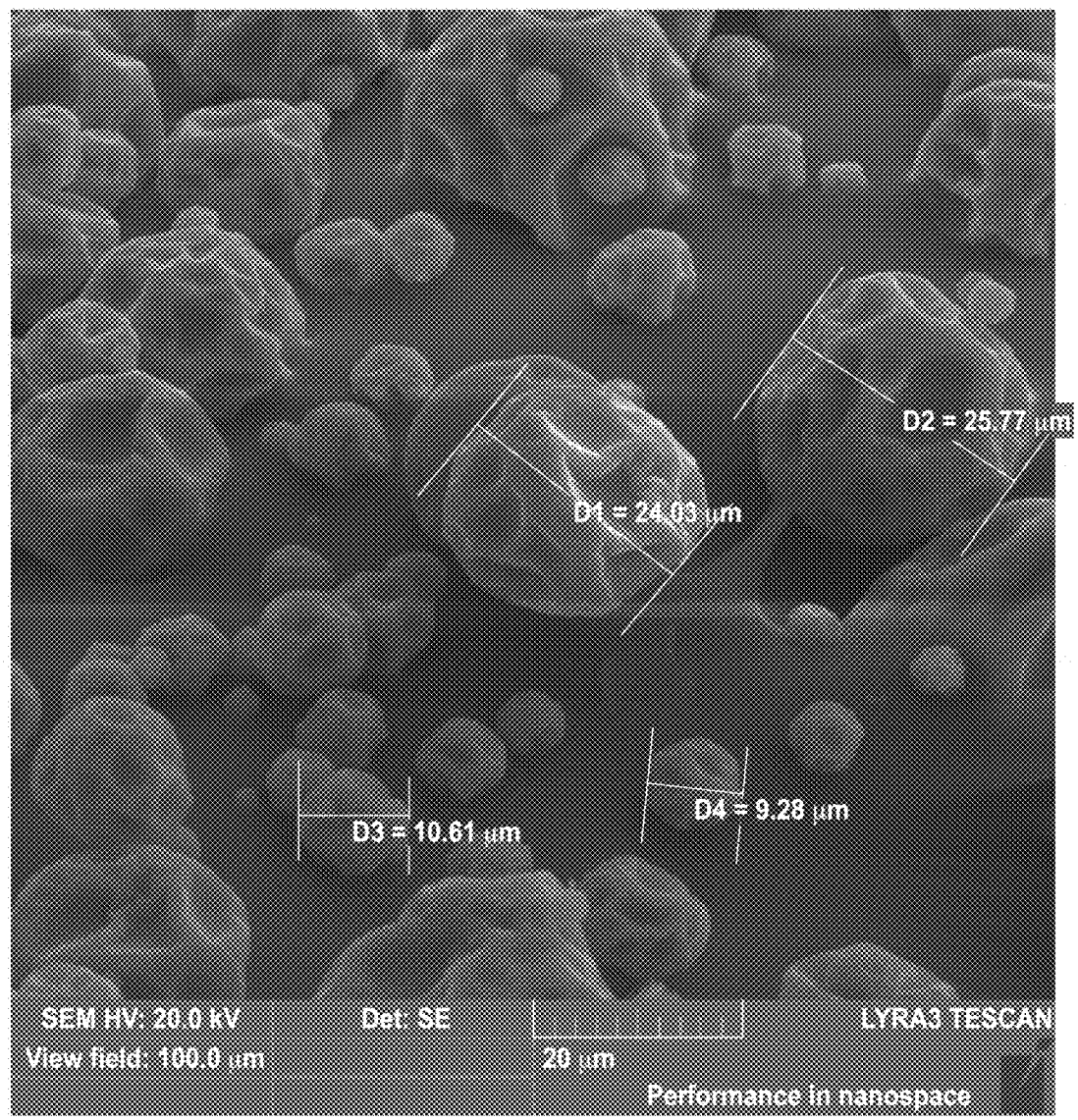
FIG. 7 is an SEM image of spray dried iohexol prepared by the spray drying method of the present invention, with characteristic dimensions indicated.

In all samples, the particles appear as separate units without mechanical binding to other particles. Particle sizes of samples 1) or 3) appear to be almost the same and show two main sizes. The first is about 10 µm and the second value is about 25 µm (see FIG. 7). The surface morphology of the particles is characterized by the presence of depressions and craters.

Figure 8:
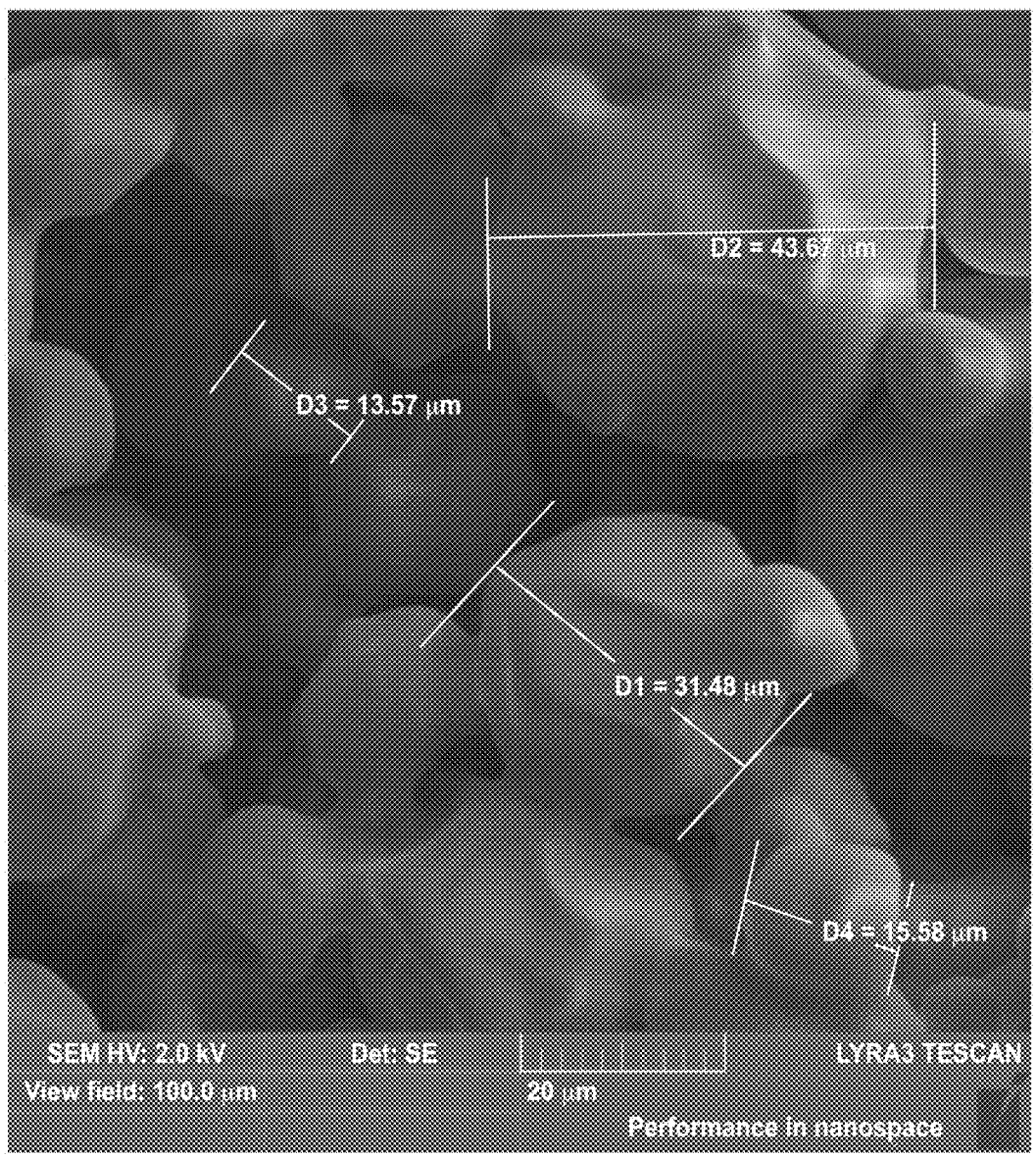
FIG. 8 is an SEM image of spray dried iohexol prepared by conventional spray drying methods, with characteristic dimensions indicated.

By contrast to samples 1) and 3), the conventional spray dried iohexol of sample 2) (FIG. 8) appears to be more uniform in distribution of the characteristic size of the particles. Also, particles of sample 2) shows a less rugged surface (shallow depressions and craters). The surface is cover with a film, similar to the sintered crystallized material of FIG. 5, i.e., after its exposure to air humidity. Sample 2) also shows multiple bridges between particles.

Figure 9A:
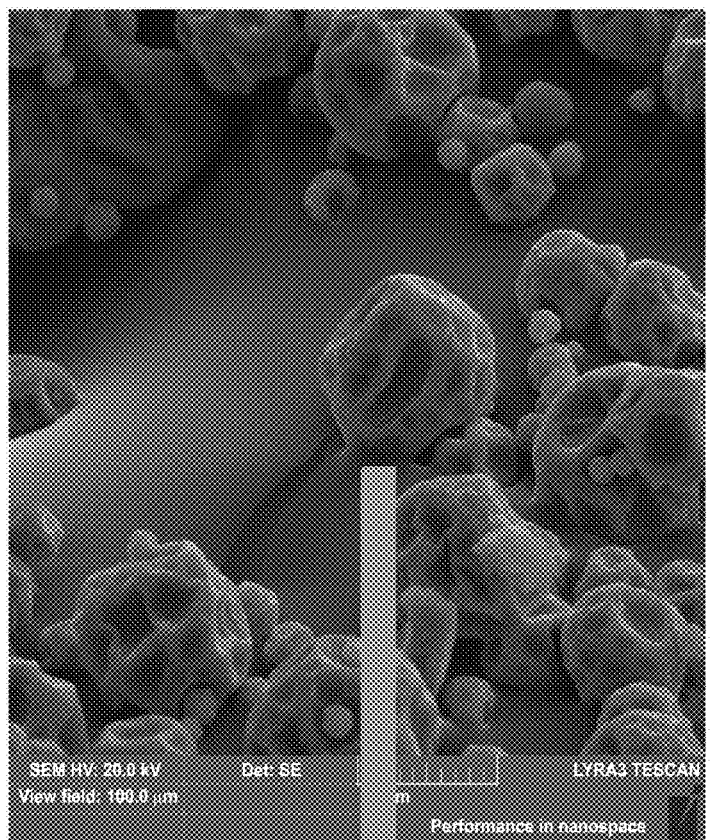
FIGS. 9A and 9B are SEM images of spray dried iohexol prepared by the spray drying methods of the present invention.
Figure 9B:
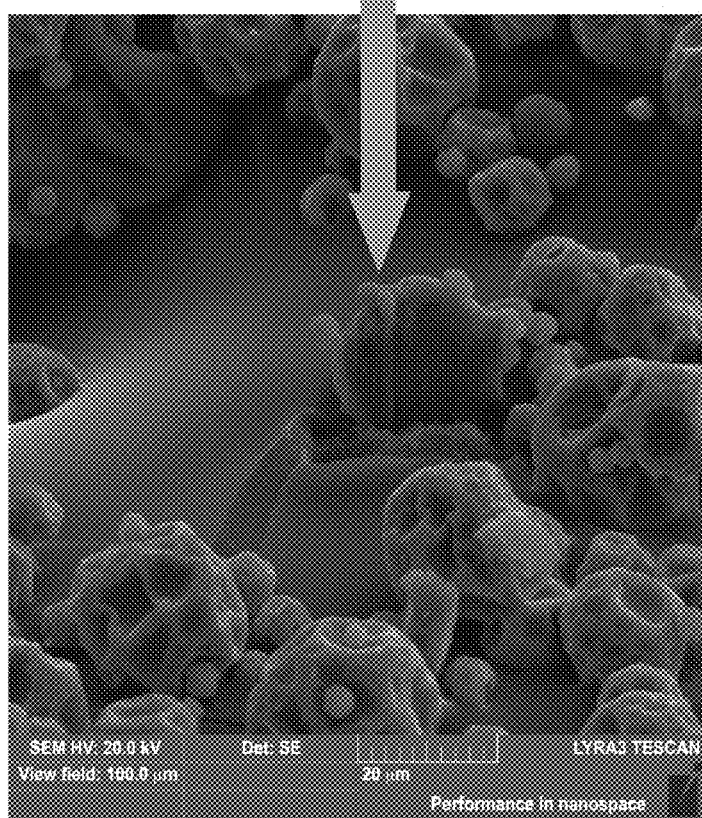
Figure 9C:
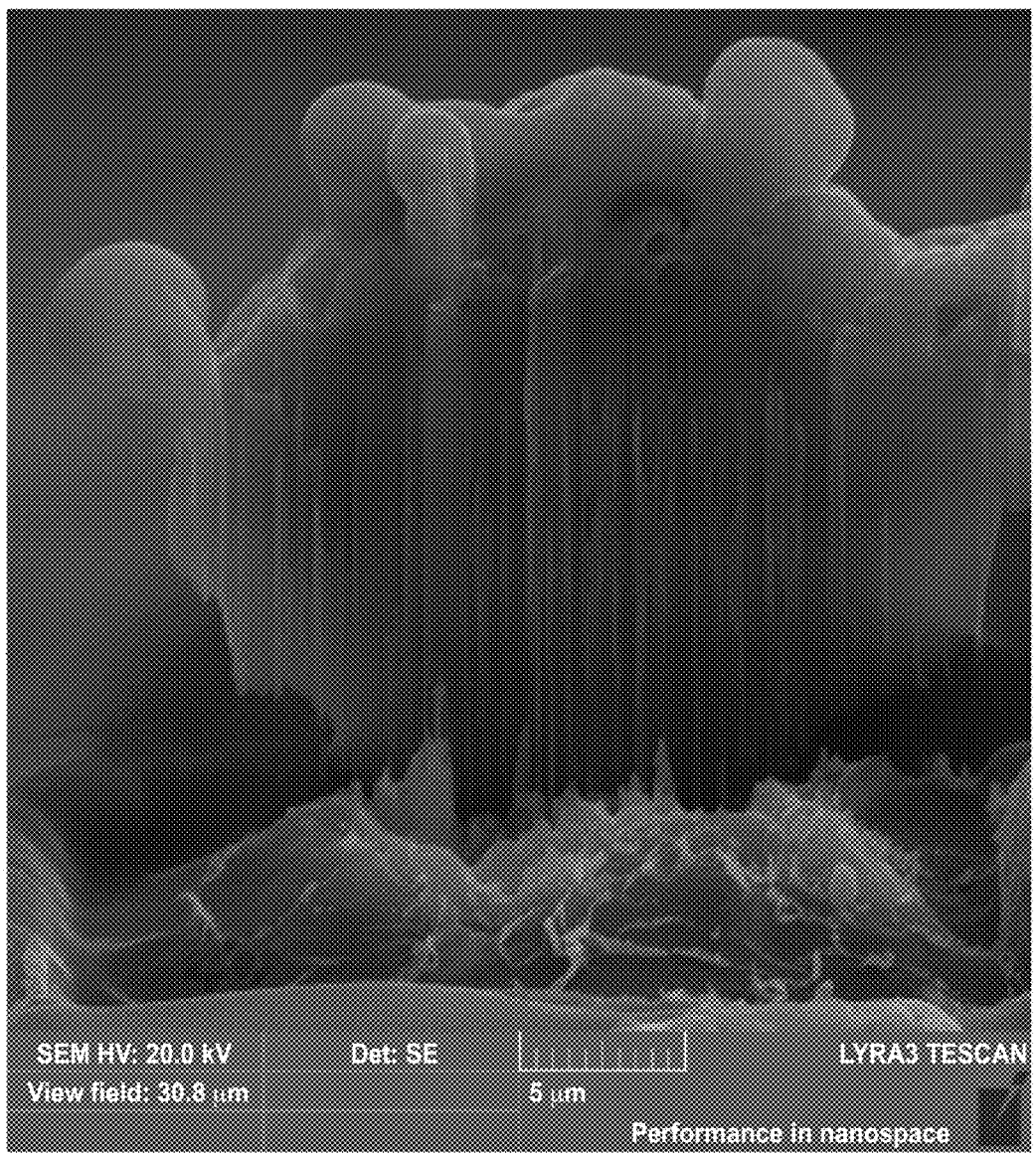
FIG. 9C is an SEM image illustrating further details of the cut surface of the spray dried iohexol particle of FIG. 9B.

In order to find possible pores or cavities inside of particles, one selected spherical particle of sample 1) was cut using an ion beam. The analysis of the SEM image (see FIGS. 9A-9C) did not show any porousity. In addition, the skeletal density (2.029 g/cm$^3$) is almost identical to the value found for crystallized iohexol, which as discussed above is demonstrably non-porous, and therefore the hypothetical existence of closed porosity in the conventionally spray dried iohexol can be excluded. The specific surface of spray dried iohexol materials was found to be less than 1 m$^2$/g, which is consistent with this observation. This value is determined by the limit of detection of the apparatus and method described herein.

A comparison of the specific amount of nitrogen desorbed from the samples provides an estimate that the specific surface area of spray dried iohexol is approximately 12 to 15 times lower than that of crystallized iohexol. These results are also consistent with theoretical values of specific surface area based on the assumption that the particles are simple geometric objects with dimensions according to SEM images.

Discussion of Values of Specific Surface Area

Experimentally obtained values of the specific surface area are very low, which is typical of macroporous to non-porous materials. Experimental specific surface area values for all samples are in good agreement with the estimated values based on SEM image analysis, (calculating the particle surface area based on the geometrical shape of particles, i.e., and assuming that the particles are not porous (confirmed by mercury porosimetry as discussed above). Individual values and comparisons of the amount of nitrogen desorption for each sample are summarized in Table 5.

TABLE 5

Values of the specific surface area of samples iohexol

| Sample | Specific Area measured [m$^2$/g] | Specific Area estimated [m$^2$/g] | Relative desorbed amount $A_d/A_{d(crystallized)}$ | Skeletal density [g/cm$^3$] |
|---|---|---|---|---|
| CRI | 2.8 | 4.0$^a$ | 1 | 2.097 |
| SDI | <1 | 0.5$^b$ | 0.08 | 2.029 |

$^a$assuming a sphere with a diameter of 3 µm
$^b$assuming two sizes of spheres (10 µm and 25 µm) with the same frequencies Based on all of the information gathered during the examination of various solid forms of iohexol and based on good agreement between estimated and measured values of specific surfaces, it is believed that iohexol particles, in all examined forms, are non-porous.

Example 4

Iohexol Purification

An aqueous solution (2200 Kg) with conductivity less than 5 µS/cm and containing 426.0 kg of raw iohexol with less than 1.5% of starting material and less than 1.6% O-alkylated related by-products is concentrated under reduced pressure to an approximate weight of 1000 Kg. 775 L of ethyl acetate is added and a portion of the water is removed via azeotropic distillation under reduced pressure. Ethyl acetate is partially (220 L) removed by distillation at reduced pressure, followed by addition of 1700 L of ethanol. A portion of the remaining ethyl acetate is removed by azeotropic distillation by means of the binary ethanol/ethyl acetate azeotrope. The resulting ethanol solution of iohexol with small amounts of ethyl acetate and water is maintained under reflux and vigorous stirring until massive crystallization occurs. The suspension is vigorously stirring for 48 hours. The mixture is cooled to 40-50° C. and the product is filtered off, washed and dried in process filter-dryer. The yield of crystallized iohexol is 320 Kg with melting point 246-254° C.

Example 5

Particles Characteristics of Iohexol Powder

Three types of solid forms of iohexol were investigated and prepared by:
Crystallized iohexol—crystallization from organic solvents, finished by drying and sieving.

Spray dryed iohexol—spray drying from aqueous solution.

All forms of iohexol were examined for the following characteristics:
Morphology of particles (aggregation, agglomeration, geometry, size)
Particle size distribution
Porosity
Specific surface area
Bulk and skeletal density
Crystallinity
Hygroscopicity
The parameters are summarized in following table 6:

TABLE 6

| Iohexol material | code | Dissolution time (s) | Particle Size distribution (μm) | | | Bulk density (g/cm3) | Skeletal density (g/cm3) | Interparticle space (% of bulk volume) | Specific surface area m²/g |
|---|---|---|---|---|---|---|---|---|---|
| | | | D10 | D50 | D90 | | | | |
| Crystallized | 01206013 | 40 | 5 | 10 | 15 | 0.56 | 2.0 | 73 | 4.00 |
| | 03302012 | 40 | 5 | 10 | 16 | 0.56 | 2.0 | 73 | 4.00 |
| Spray dryed | 03202012/1 | 60 | 9 | 14 | 22 | 0.90 | 2.0 | 56 | 0.50 |
| | 03202012/8 | 40 | 7 | 12 | 19 | 0.90 | 2.0 | 56 | 0.50 |
| | 03202012/9 | 60 | 11 | 20 | 35 | 0.90 | 2.0 | 56 | 0.50 |
| | Conventional Sample #1 | 90 | 7 | 27 | 61 | 0.90 | 2.0 | 56 | 0.50 |
| | Conventional Sample #2 | 90 | 7 | 29 | 66 | 0.90 | 2.0 | 56 | 0.50 |

Crystallinity—the crystalline character of crystallized iohexol was confirmed by XRPD. Spray dried iohexol was found to be essentially amorphous.

Particle morphology—crystallized iohexol forms agglomerates of particles of spherical/ellipsoidal shape having a characteristic dimension of the individual particles approximately 0.5-3 μm. Particles are organized in agglomerates with average D50 of 10 μm.

Spray dried iohexol is formed of spherical units with or without mechanical binding to other particles, depending on drying conditions. Also, the particle size distribution varies in D50 from 14 to 29 μm. All particles are characterized by the presence of depressions and craters.

Skeletal density, bulk density—All forms of iohexol have substantially the same skeletal density, which is evidence that the mass of the interior of the particles is organized in a similar manner. Crystallized iohexol exhibited lower bulk density than spray dried iohexol. Surprisingly, the bulk density was found to play an important role in the dissolution characteristics of iohexol.

Porosity—all forms of iohexol were found to be nonporous. Specific surface areas of all examined forms are relatively small due to the absence of pores; however the difference between crystallized iohexol and spray dried iohexol is significant. Crystallized iohexol has a specific surface area of about 4 m²/g, and spray dried iohexol is a specific surface area of about 0.5 m²/g.

Dissolution time—the time required for complete dissolution for all forms of iohexol was tested. The values obtained vary from 30 to 90 seconds.

Example 6

Figure 10B:
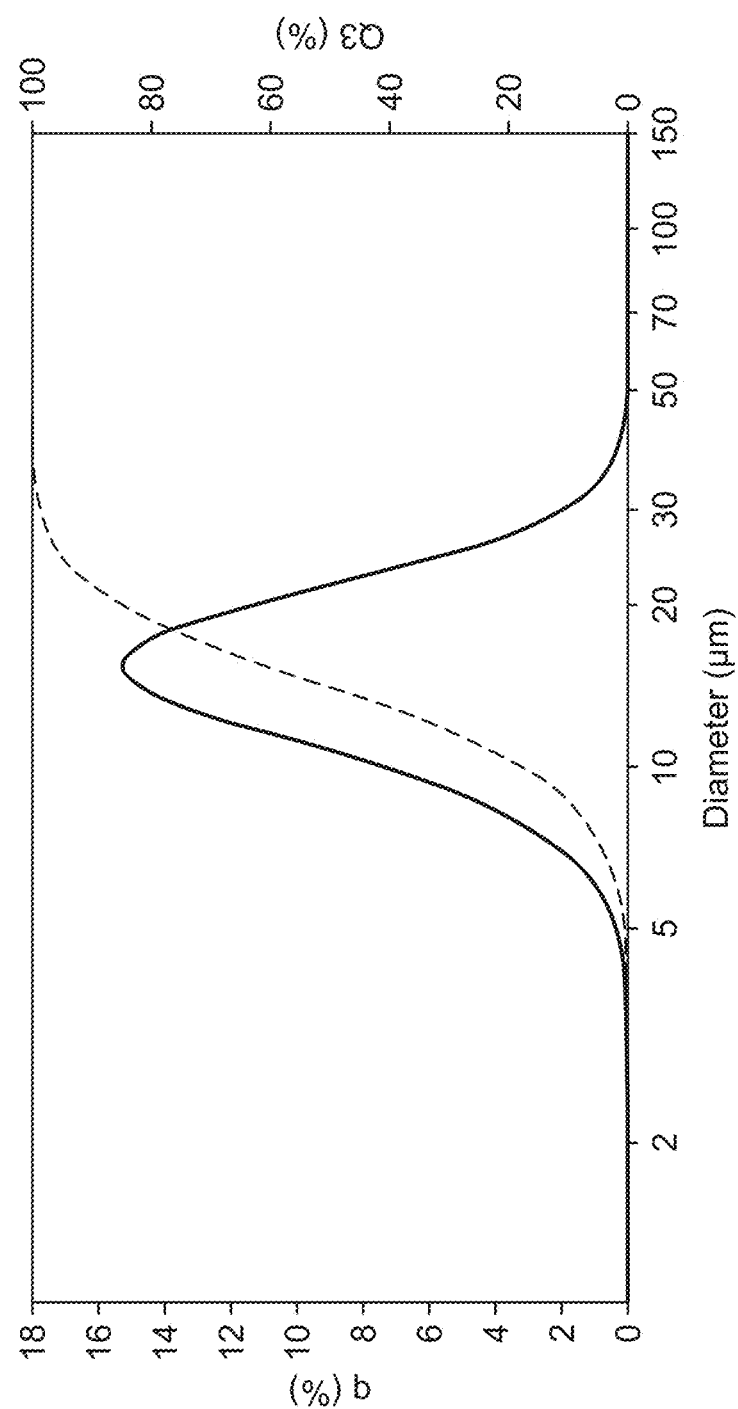
FIG. 10B is a plot of particle size distribution for particle code 03202012/1 from FIG. 10A.
Figure 10C:
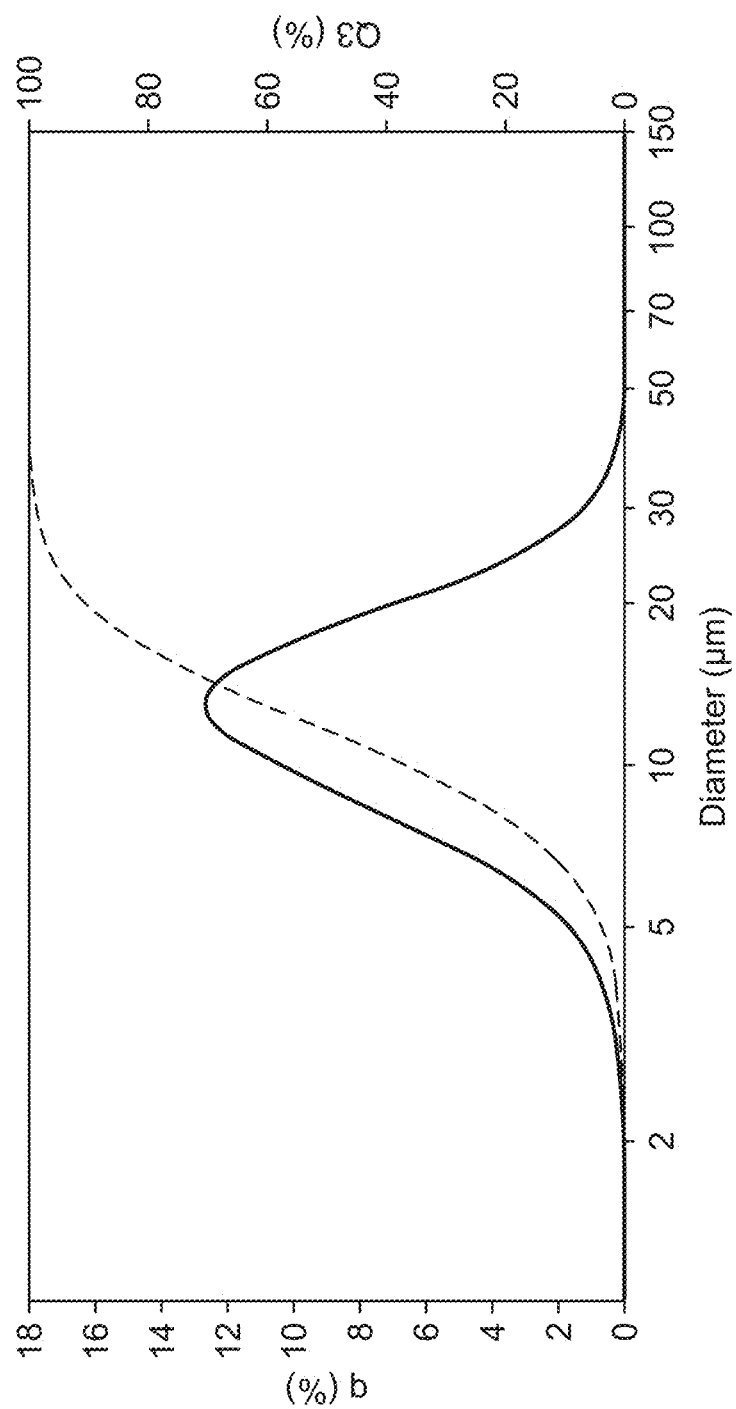
FIG. 10C is a plot of particle size distribution for particle code 03202012/8 from FIG. 10A.
Figure 10D:
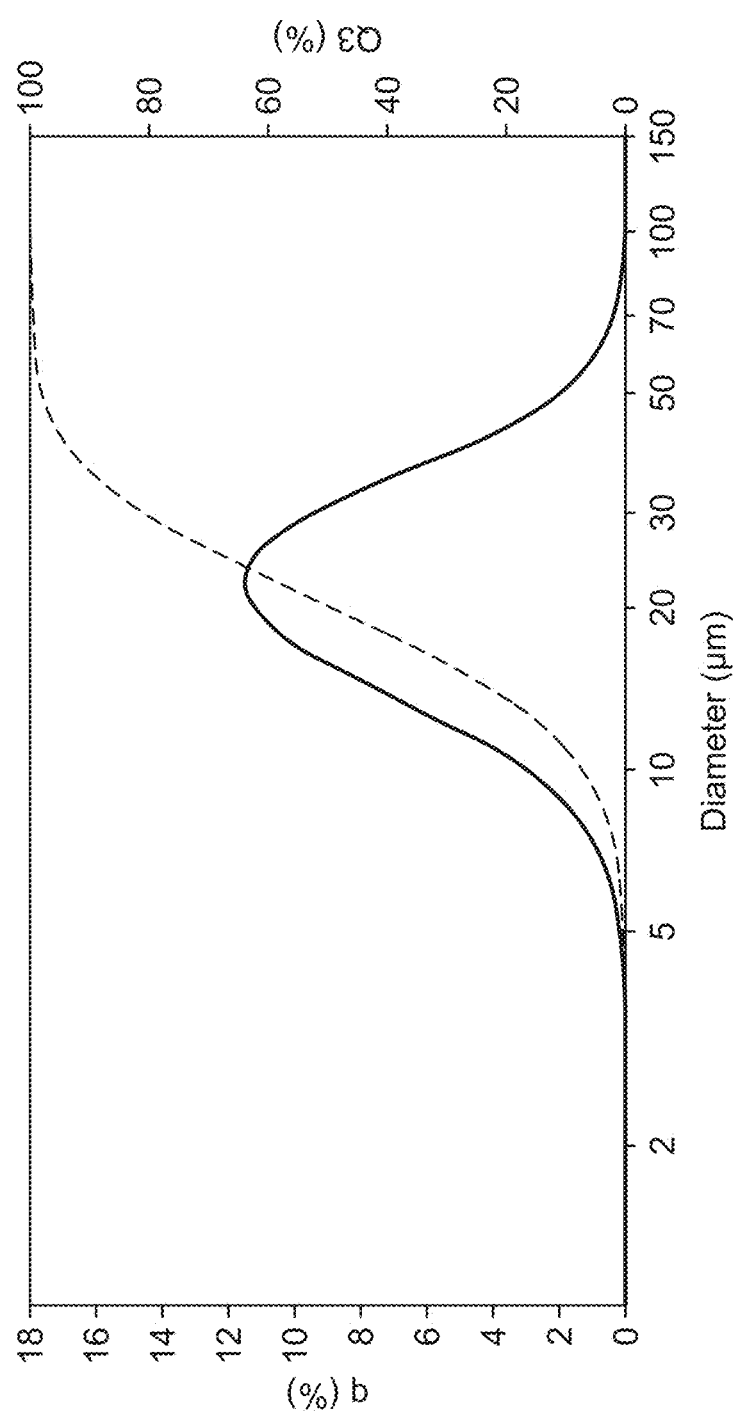
FIG. 10D is a plot of particle size distribution for particle code 03202012/9 from FIG. 10A.
Figure 10E:
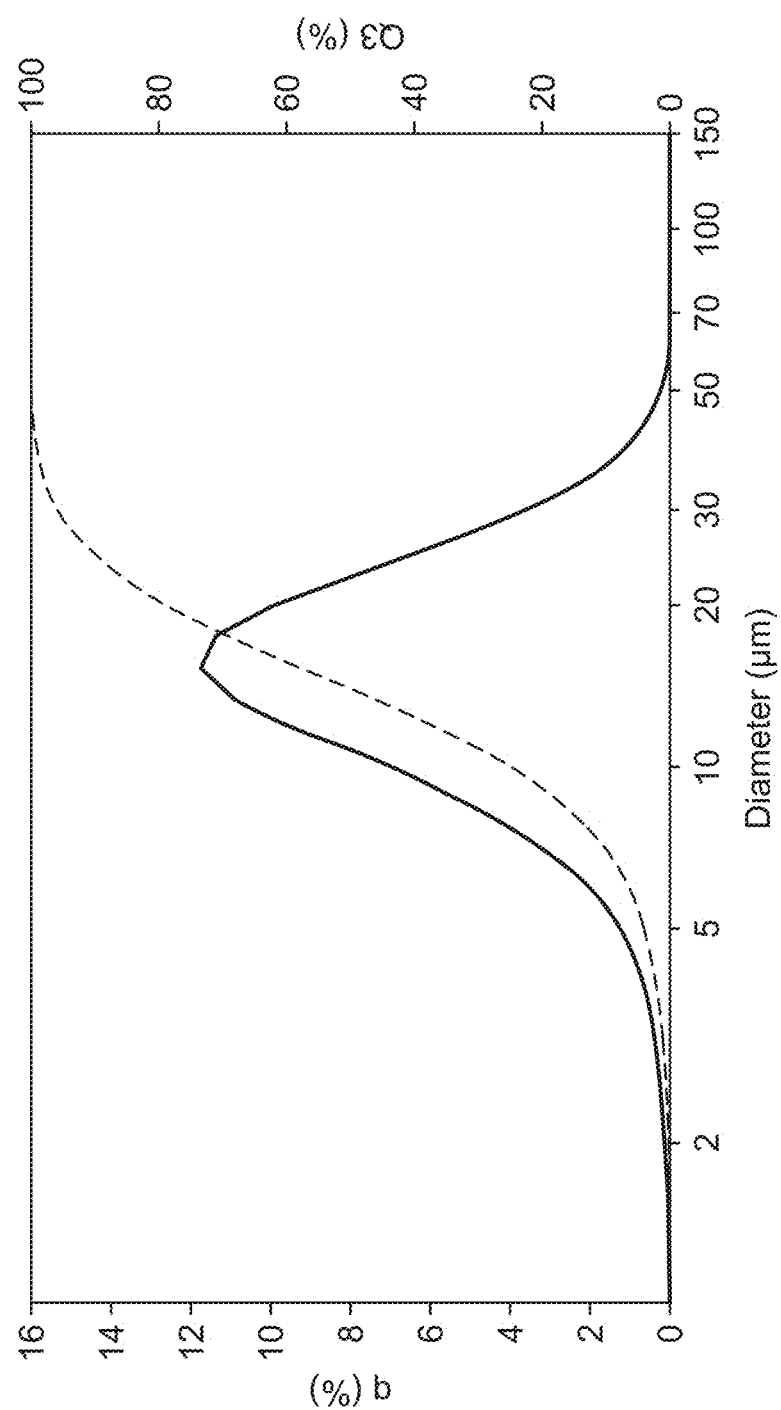
FIG. 10E is a plot of particle size distribution for Conventional Sample #1 from FIG. 10A.
Figure 10F:
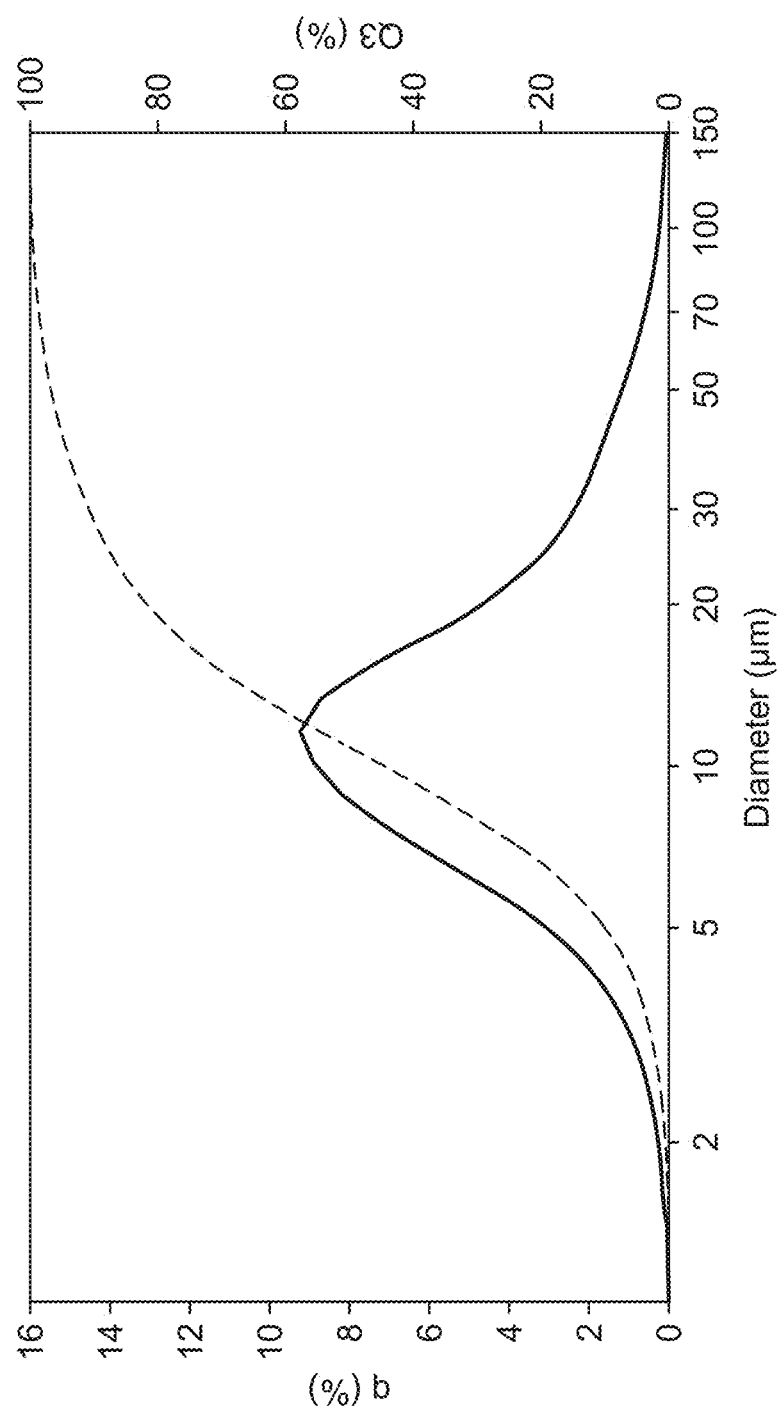
FIG. 10F is a plot of particle size distribution for Conventional Sample #2 from FIG. 10A.

Effect of Spray Drier Characteristics on Particle Size Distribution for Spray Dried Iohexol See FIG. 10A for particle characteristics of spray dried iohexol prepared with varying spray drying parameters.

$T_{INLET}$(° C.)—air temperature when entering into spray dryer.
$T_{OUTLET}$(° C.)—air temperature when leaving spray dryer
Atomizer rpm—revolution of centrifugal atomizer per minute
Input concentration of iohexol solution % (w/w)—Concentration of starting solution of iohexol pumped to atomizer of spray dryer
FIGS. 10B-10F illustrate particle size distributions for the resulting iohexol compositions for each initial iohexol solution listed in the Table of FIG. 10A.

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. The embodiments have been particularly shown and described, but it will be understood that various changes in form and details may be made. For example, although various embodiments have been described as having particular features and/or combinations of components, other embodiments are possible having any combination or sub-combination of any features and/or components from any of the embodiments described herein.

What is claimed is:
1. A method of preparing iohexol crystals, comprising:
crystallizing iohexol from a mixture of solvents comprising alcohol, alkyl acetate and water,
wherein said crystallizing comprises:
(a) heating a solution of iohexol in the mixture of solvents to reflux, with agitation;
(b) removing at least a portion of one or more of the alcohol, alkyl acetate, and water by distilling the solution of iohexol;
(c) maintaining the solution of iohexol from step (b) with agitation at reflux, whereby a suspension of crystals of substantially exo iohexol are formed;
(d) cooling the suspension of step (c) to about 40-50° C., with agitation; and
(e) filtering and drying the suspension.

2. The method of claim 1, wherein said distilling is azeotropic distillation and provides a solution comprising about 20-25% (w/v) of iohexol, 95-97% alcohol, 2-5% of alkyl acetate, and 0.1-2% water.

* * * * *